US012245740B2

(12) United States Patent
D'Lima et al.

(10) Patent No.: US 12,245,740 B2
(45) Date of Patent: Mar. 11, 2025

(54) SYSTEMS AND METHODS TO REPAIR TISSUE DEFECTS

(71) Applicant: SCRIPPS HEALTH, San Diego, CA (US)

(72) Inventors: Darryl D. D'Lima, San Diego, CA (US); Clifford W. Colwell, Jr., La Jolla, CA (US)

(73) Assignee: SCRIPPS HEALTH, San Diego, CA (US)

( * ) Notice: Subject to any disclaimer, the term of this patent is extended or adjusted under 35 U.S.C. 154(b) by 44 days.

(21) Appl. No.: 18/045,377

(22) Filed: Oct. 10, 2022

(65) Prior Publication Data

US 2023/0233058 A1 Jul. 27, 2023

Related U.S. Application Data

(63) Continuation of application No. 16/304,618, filed as application No. PCT/US2017/034539 on May 25, 2017, now Pat. No. 11,497,831.

(Continued)

(51) Int. Cl.
*A61L 27/20* (2006.01)
*A61B 1/00* (2006.01)
(Continued)

(52) U.S. Cl.
CPC ............ *A61B 1/00009* (2013.01); *A61B 1/00* (2013.01); *A61B 34/30* (2016.02); *A61B 90/00* (2016.02);
(Continued)

(58) Field of Classification Search
CPC ....... A61B 34/30; A61B 17/3468; A61B 1/00; A61B 1/00009; A61B 2017/00969;
(Continued)

(56) References Cited

U.S. PATENT DOCUMENTS 5,425,723 A 6/1995 Wang
5,526,027 A 6/1996 Wade et al.
(Continued)

FOREIGN PATENT DOCUMENTS

EP 1027989 A2 8/2000
EP 1232863 A1 8/2002
(Continued)

OTHER PUBLICATIONS

Cui et al. (Journal of Visualized Experiments 2014;88:e51294:5 pages) (Year: 2014).*
(Continued)

*Primary Examiner* — Ernst V Arnold
(74) *Attorney, Agent, or Firm* — WILSON SONSINI GOODRICH & ROSATI

(57) ABSTRACT

Methods of bioprinting a bio-ink construct on an internal tissue defect or a chondral defect during a minimally invasive surgery on an individual in need thereof are provided, comprising: visualizing the defect; positioning a bioprinter comprising a printhead within proximity of or in contact with the defect; and ejecting a bio-ink from the printhead onto the defect to form a bio-ink layer, thereby generating a bio-ink construct. Further provided are systems for bioprinting a bio-ink construct on an internal tissue defect during a minimally invasive surgery on an individual in need thereof, comprising a control system, an endoscope, and a bioprinter comprising a printhead.

20 Claims, 5 Drawing Sheets

Related U.S. Application Data

(60) Provisional application No. 62/341,914, filed on May 26, 2016.

(51) Int. Cl.
*A61B 34/30* (2016.01)
*A61B 90/00* (2016.01)
*A61F 2/08* (2006.01)
*A61F 2/30* (2006.01)
*A61L 27/02* (2006.01)
*A61L 27/24* (2006.01)
*A61L 27/36* (2006.01)
*A61M 5/142* (2006.01)
*A61M 5/20* (2006.01)
*B29C 64/112* (2017.01)
*B33Y 10/00* (2015.01)
*B33Y 70/00* (2020.01)
*C12N 5/077* (2010.01)
*A61B 17/00* (2006.01)

(52) U.S. Cl.
CPC .......... *A61F 2/0805* (2013.01); *A61F 2/0811* (2013.01); *A61F 2/30756* (2013.01); *A61F 2/3094* (2013.01); *A61L 27/025* (2013.01); *A61L 27/20* (2013.01); *A61L 27/24* (2013.01); *A61L 27/3604* (2013.01); *A61L 27/3608* (2013.01); *A61L 27/3612* (2013.01); *A61M 5/14212* (2013.01); *A61M 5/20* (2013.01); *B29C 64/112* (2017.08); *B33Y 10/00* (2014.12); *B33Y 70/00* (2014.12); *C12N 5/0654* (2013.01); *C12N 5/0655* (2013.01); *A61B 2017/00969* (2013.01); *A61B 2090/395* (2016.02); *A61F 2002/30962* (2013.01); *A61L 2430/06* (2013.01)

(58) Field of Classification Search
CPC ............... A61B 2090/395; A61B 90/00; A61F 2002/30962; A61F 2/30756; A61F 2/3094; A61F 2/0805; A61F 2/0811; A61L 2430/06; A61L 27/025; A61L 27/20; A61L 27/24; A61L 27/3604; A61L 27/3608; A61L 27/3612; A61M 5/14212; A61M 5/20

See application file for complete search history.

(56) References Cited

U.S. PATENT DOCUMENTS

| | | | |
|---|---|---|---|
| 6,077,251 | A | 6/2000 | Ting et al. |
| 6,517,521 | B1 | 2/2003 | Ly |
| 6,733,479 | B1 | 5/2004 | Ott |
| 7,767,452 | B2 | 8/2010 | Kleinsek |
| 8,323,881 | B2 | 12/2012 | Fujisato et al. |
| 9,393,364 | B2 | 7/2016 | Fischer, Jr. |
| 9,498,271 | B2 | 11/2016 | Osborne et al. |
| 11,369,465 | B2 | 6/2022 | D'Lima et al. |
| 11,497,831 | B2 | 11/2022 | D'Lima et al. |
| 2002/0177822 | A1 | 11/2002 | St. Cyr et al. |
| 2002/0177903 | A1 | 11/2002 | Geistlich et al. |
| 2003/0049839 | A1 | 3/2003 | Romero-Ortega et al. |
| 2003/0065400 | A1 | 4/2003 | Beam et al. |
| 2003/0100824 | A1 | 5/2003 | Warren et al. |
| 2003/0175410 | A1 | 9/2003 | Campbell et al. |
| 2004/0005295 | A1 | 1/2004 | Lee et al. |
| 2004/0193097 | A1 | 9/2004 | Hofmann et al. |
| 2004/0237822 | A1 | 12/2004 | Boland et al. |
| 2005/0209564 | A1 | 9/2005 | Bonner et al. |
| 2005/0226855 | A1 | 10/2005 | Alt et al. |
| 2006/0156978 | A1 | 7/2006 | Lipson et al. |
| 2008/0166329 | A1 | 7/2008 | Sung et al. |
| 2008/0294096 | A1 | 11/2008 | Uber, III et al. |
| 2009/0117087 | A1 | 5/2009 | Carroll et al. |
| 2009/0239302 | A1 | 9/2009 | Decher et al. |
| 2010/0076397 | A1 | 3/2010 | Reed et al. |
| 2010/0178274 | A1 | 7/2010 | Sekiya et al. |
| 2010/0236481 | A1 | 9/2010 | O'Brien et al. |
| 2011/0136162 | A1 | 6/2011 | Sun et al. |
| 2011/0234668 | A1 | 9/2011 | Hoisington et al. |
| 2012/0089238 | A1 | 4/2012 | Kang et al. |
| 2013/0041380 | A1 | 2/2013 | Sengun et al. |
| 2014/0012225 | A1 | 1/2014 | Yoo et al. |
| 2015/0105891 | A1 | 4/2015 | Golway et al. |
| 2015/0224291 | A1 | 8/2015 | Guillemot et al. |
| 2019/0008998 | A1 | 1/2019 | Cui et al. |
| 2022/0331086 | A1 | 10/2022 | D'Lima et al. |
| 2023/0028989 | A1 | 1/2023 | D'Lima et al. |

FOREIGN PATENT DOCUMENTS

| | | |
|---|---|---|
| EP | 1374941 B1 | 8/2006 |
| EP | 2343415 A2 | 7/2011 |
| GB | 2343415 A | 5/2000 |
| JP | 2002254654 A | 9/2002 |
| JP | 2010501547 A | 1/2010 |
| JP | 2011255513 A | 12/2011 |
| JP | 2016513979 A | 5/2016 |
| RU | 2733955 C1 | 10/2020 |
| WO | WO-9922683 A1 | 5/1999 |
| WO | WO-2009049823 A1 | 4/2009 |
| WO | WO-2011066577 A1 | 6/2011 |
| WO | WO-2011107599 A1 | 9/2011 |
| WO | WO-2014110590 A1 | 7/2014 |
| WO | WO-2015017579 A1 | 2/2015 |
| WO | WO-2015066705 A1 | 5/2015 |
| WO | WO-2015175880 A1 | 11/2015 |
| WO | WO-2015179572 A1 | 11/2015 |
| WO | WO-2016164566 A1 | 10/2016 |
| WO | WO-2017040975 A1 | 3/2017 |
| WO | WO-2017080646 A1 | 5/2017 |
| WO | WO-2017205663 A1 | 11/2017 |
| WO | WO-2018083010 A1 | 5/2018 |
| WO | WO-2018185755 A1 | 10/2018 |
| WO | WO-2021113301 A1 | 6/2021 |

OTHER PUBLICATIONS

Pongphantarak, S. ([Online] retrieved on Sep. 3, 2024 from: (https://www.samitivejhospitals.com/article/detail/natural-orifice-transluminal-endoscopic-surgery-notes; Aug. 26, 2016; 4 pages). (Year: 2016).*
Nomura et al. (Gynecology and Minimally Invasive Therapy 2013;2:85-88). (Year: 2013).*
Badylak et al. Whole-organ tissue engineering: decellularization and recellularization of three-dimensional matrix scaffolds. Annu Rev Biomed Eng 13 (2011): 27-53.
Bartolovic et al. The differentiation and engraftment potential of mouse hematopoietic stem cells is maintained after bio-electrospray. Analyst 135:157-164 (2010).
Bone and Joint Regeneration Technology. National Institute of Advanced Industrial Science and Technology Today. Available at https://www.aist.go.jp/Portals/0/resource_images/aist_e/research_results/publications/pamphlet/today/b_regeneration_e.pdf (16 pgs) (2006).
Brinkman et al. Photo-cross-linking of type I collagen gels in the presence of smooth muscle cells: mechanical properties, cell viability, and function. Biomacromulecules 4:890-895 (2003).
Chiu et al. Functionalization of poly(L-lactide) nanofibrous scaffolds with bioactive collagen molecules. J Biomed Mater Res 83(4):1117-1127 (2007).
Cui et al. Accelerated myotube formation using bioprinting technology for biosensor applications. Biotechnol Lett 35(3):315-321 (2013).
Cui et al. Direct Human Cartilage Repair Using Three-Dimensional Bioprinting Technology. Tissue Engineering Part A 18(11-12):1304-1312 (2012).

(56) References Cited

OTHER PUBLICATIONS

Cui et al. Synergistic Action of Fibroblast Growth Factor-2 and Transforming Growth Factor-beta1 Enhances Bioprinted Human Neocartilage Formation. Biotechnol Bioeng 109(9):2357-2368 (2012).
Cui et al. Thermal Inkjet Printing in Tissue Engineering and regenerative Medicine. Recent Pat Drug Deliv Formul 6(2):149-155 (2012).
Gruene et al. Laser printing of stem cells for biofabrication of scaffold-free autologous grafts. Tissue Engineering: Part C Methods 17(1):79-89 (2011).
Gupta et al. In Situ Photo-Cross-Linking of Cinnamate Functionalized Poly(methyl methacrylate-co-2-hydroxyethyl acrylate) Fibers during Electrospinning. Macromolecules 37(24):9211-9218 (2004).
Haslauer et al. Collagen-PCL Sheath-Core Bicomponent Electrospun Scaffolds Increase Osteogenic Differentiation and Calcium Accretion of Human Adipose-Derived Stem Cells. J Biomater Sci Polym Ed 22(13):1695-1712 (2011).
Li et al. Carbodiimide crosslinked collagen from porcine dermal matrix for high-strength tissue engineering scaffold. Int J Biol Macromol 61:69-74 (2013).
Li et al. Electrospun polyacrylonitrile nanofiber yarn prepared by funnel-shape collector Materials Letters 79:245-247 (2012).
Matsusaki et al. Three-dimensional human tissue chips fabricated by rapid and automatic inkjet cell printing. Adv Healthcare Mater 2(4):534-539 (2013).
O'Connell et al. Development of the Biopen: a handheld device for surgical printing of adipose stem cells at a chondral wound site. Biofabrication 8(1):015019 (2016).
Pak et al., Regenerative repair of damaged meniscus with autologous adipose tissue-derived stem cells. BioMed Research International 2014:436029 (2014).
PCT/US2014/011525 International Search Report and Written Opinion dated May 13, 2014.
PCT/US2017/034539 International Search Report and Written Opinion dated Sep. 8, 2017.
PCT/US2020/062805 International Search Report and Written Opinion dated Mar. 9, 2021.
Pescosolido et al. Hyaluronic acid and dextran-based semi-IPN hydrogels as biomaterials for bioprinting. Biomacromolecules 12(5):1831-1838 (2011).
Rye. Microneedle Arrays for Injection Seeding of Tissue Engineered Scaffolds. Thesis (81 pgs) (2014).
Sahoo et al. Bio-electrospraying: A potentially safe technique for delivering progenitor cells. Biotechnol Bioeng 106(4):690-698 (2010).
Schuurman et al. Bioprinting of hybrid tissue constructs with tailorable mechanical properties. Biofabrication 3(2):021001 (7 pgs.) (2011).
Shafiq et al. Decellularized human cornea for reconstructing the corneal epithelium and anterior stroma. Tissue Eng Part C Methods 18(5):340-348 (2012).
Shields et al. Mechanical Properties and Cellular Proliferation of Electrospun Collagen Type II. Tissue Engineering 10(9/10):1510-1517 (2004).
Song et al., Engineered 3D tissue models for cell-laden microfluidic channels. Analytical and Bioanalytical Chemistry 395:185-193 (2009).
Song et al. Sodium alginate hydrogel-based bioprinting using a novel multinozzle bioprinting system. Artif Org 35(11):1132-1136 (2011).
Srouji et al. 3-D Nanofibrous electrospun multilayered construct is an alternative ECM mimicking scaffold. J Mater Sci Mater Med 19(3):1249-1255 (2008).
Stankus et al. Fabrication of cell microintegrated blood vessel constructs through electrohydrodynamic atomization. Biomaterials. 28:2738-2746 (2007).
Tsuda. Hone Kyushu Yokuseiyaku Koho to shite no Hakotsu Saibo Keisei Yokusei Inshi OCIF/OPG, Ko-RANKL Kotai, Oyobi sono Hoka no RANKL/RANK System Modulator J. Jpn Orthop Assoc. 78(8):1-P3-5 (2005) (w/English translation).
U.S. Appl. No. 14/759,398 Office Action dated Mar. 16, 2021.
U.S. Appl. No. 14/759,398 Office Action dated Mar. 22, 2019.
U.S. Appl. No. 14/759,398 Office Action dated Mar. 30, 2020.
U.S. Appl. No. 14/759,398 Office Action dated May 24, 2018.
U.S. Appl. No. 14/759,398 Office Action dated Nov. 2, 2017.
U.S. Appl. No. 14/759,398 Office Action dated Oct. 14, 2020.
U.S. Appl. No. 14/759,398 Office Action dated Sep. 24, 2019.
Xu et al. Hybrid printing of mechanically and biologically improved constructs for cartilage tissue engineering applications. Biofabrication 5(1):015001 (10 pgs) (2012).
Yamaguchi et al. Cell patterning through inkjet printing of one cell per droplet. Biofabrication 4(4):045005 (8 pgs) (2012).
Yan et al. Laser-assisted printing of alginate long tubes and annular constructs. Biofabrication 5(1):015002 (8 pgs) (2013).
Yu et al., Decellularized scaffolds in regenerative medicine. Oncotarget 7(36):58671-58683 (2016).
Zhang et al. Characterization of the surface biocompatibility of the electrospun PCL-collagen nanofibers using fibroblasts. Biomacromolecules 6:2583-2589 (2005).
Zhao et al. Biodegradable fibrous scaffolds composed of gelatin coated poly(epsilon-caprolactone) prepared by coaxial electrospinning. J Biomed Mater Res A 83(2):372-382 (2007).

\* cited by examiner

SYSTEMS AND METHODS TO REPAIR TISSUE DEFECTS

CROSS-REFERENCE

This application is a continuation of U.S. patent application Ser. No. 16/304,618, filed Nov. 26, 2018, now U.S. Pat. No. 11,497,831, issued Nov. 15, 2022, which is a 371 U.S. National Stage Application of PCT/US2017/034539, filed May 25, 2017, which claims the benefit of U.S. Provisional Application No. 62/341,914, filed on May 26, 2016, all of which are incorporated herein by reference in their entirety.

SUMMARY OF THE INVENTION

Disclosed herein, in certain embodiments, are methods of bioprinting a bio-ink construct on an internal tissue defect during a minimally invasive surgery on an individual in need thereof, comprising: (a) visualizing the internal tissue defect; (b) positioning a bioprinter comprising a printhead within proximity of or in contact with the internal tissue defect; and (c) ejecting a bio-ink from the printhead onto the internal tissue defect to form a bio-ink layer, thereby generating a bio-ink construct. In some embodiments, the bio-ink construct comprises a plurality of bio-ink layers. In some embodiments, the bio-ink construct is a live tissue. In some embodiments, the printhead comprises a needle, an extended cylinder, a fluid line, a print nozzle, or a plurality of print nozzles. In some embodiments, each print nozzle of the plurality of print nozzles is independently controlled and actuated. In some embodiments, each print nozzle of the plurality of print nozzles is actuated to eject an individual droplet of the bio-ink. In some embodiments, the plurality of print nozzles ejects the individual droplet simultaneously. In some embodiments, the plurality of print nozzles ejects the individual droplet in a specified sequence. In some embodiments, the printhead ejects the bio-ink continuously. In some embodiments, the bio-ink comprises a plurality of cells, a component of extracellular matrix, a synthetic polymer, a natural polymer, a cross-linking agent, a photoinitiator, or a combination thereof. In some embodiments, the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, kidney cells, hepatic cells, pancreatic cells, immune cells, stem cells, germ cells, nurse cells, interstitial cells, stellate cells and progenitors thereof. In some embodiments, the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, and progenitors thereof. In some embodiments, the plurality of cells comprises chondrocytes. In some embodiments, the component of extracellular matrix comprises collagen, elastin, fibrillin, fibronectin, laminin, fibrinogen, tenascin, thrombospondin, integrin, hyaluronic acid, heparin, heparin sulfate, chondroitin sulfate, keratin sulfate, dermatan sulfate, or a combination thereof. In some embodiments, the synthetic polymer is polyethylene glycol (PEG), a PEG macromere, polyethylene glycol methacrylate (PEGMA), polyethylene dimethacrylate (PEDGMA), poly (hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide, or a combination thereof. In some embodiments, the natural polymer is alginate, cellulose, gelatin, pectin, agarose, chitosan, or a combination thereof. In some embodiments, the cross-linking agent comprises calcium chloride, calcium sulfate, calcium carbonate, calcium ($Ca^{2+}$), magnesium ($Mg^{2+}$), glutaraldehyde, genipin, nordihydroguaiaretic acid, tannin acid, procyanidins, glycosaminoglycan (GAG), 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), or a combination thereof. In some embodiments, the method comprises polymerizing the bio-ink. In some embodiments, polymerizing the bio-ink comprises cross-linking the bio-ink. In some embodiments, cross-linking the bio-ink comprises delivering the cross-linking agent by the printhead to the bio-ink. In some embodiments, cross-linking the bio-ink comprises applying UV light from a light source to the bio-ink. In some embodiments, cross-linking the bio-ink comprises applying heat to the bio-ink. In some embodiments, the bioprinter comprises a second printhead. In some embodiments, the method comprises positioning a second bioprinter comprising a printhead within proximity of or in contact with the internal tissue defect. In some embodiments, the method comprises ejecting a second bio-ink from the printhead of the second bioprinter onto the internal tissue defect to form a second bio-ink layer. In some embodiments, the method comprises controlling the bioprinter with a control system. In some embodiments, the control system comprises a computer system. In some embodiments, the control system comprises a robotic arm operatively connected to the computer system. In some embodiments, the robotic arm is coupled to a body part of the individual. In some embodiments, the robotic arm positions the bioprinter. In some embodiments, the bioprinter is moved along an X, Y, or Z axis, or a combination thereof. In some embodiments, the bioprinter is rotated around the X, Y, or Z axis, or a combination thereof. In some embodiments, the control system controls a bio-ink printing parameter. In some embodiments, the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof. In some embodiments, visualizing the internal tissue defect occurs before, during, or after ejecting the bio-ink. In some embodiments, visualizing the internal tissue defect comprises imaging the internal tissue defect. In some embodiments, the method comprises positioning an endoscope within proximity of the internal tissue defect. In some embodiments, the endoscope visualizes the internal tissue defect. In some embodiments, the internal tissue defect is selected from a damaged tissue, eroded tissue, diseased tissue or degenerated tissue. In some embodiments, the internal tissue defect is in an internal tissue selected from bone, muscle, nerves, brain, eye, pancreas, spleen, cartilage, thyroid, adipose, sinus, esophagus, kidney, heart, lung, intestine, stomach, colon, rectum, breast, ovary, uterus, cervix, prostate, bladder or liver. In some embodiments, the internal tissue defect is selected from a vascular defect, a chondral defect, a muscular defect, an intestinal defect, a neuronal defect, a reproductive defect, a pancreatic defect, or an ocular defect. In some embodiments, the internal tissue defect comprises a chondral defect. In some embodiments, the chondral defect is in a joint selected from a knee joint, a hip joint, an elbow joint, a shoulder joint, a wrist joint, a spine joint, a finger joint, an ankle joint, or a foot joint. In some embodiments, the chondral defect is in a knee joint. In some embodiments, the chondral defect is an osteochondral defect.

Disclosed herein, in certain embodiments, are methods of bioprinting a bio-ink construct on a chondral defect during a minimally invasive surgery on an individual in need thereof comprising: (a) visualizing the chondral defect; (b) positioning a bioprinter comprising a printhead within proximity of or in contact with the chondral defect; and (c) ejecting a bio-ink from the printhead onto the chondral defect to form a bio-ink layer, thereby generating a bio-ink construct. In some embodiments, the bio-ink construct comprises a plurality of bio-ink layers. In some embodiments, the bio-ink construct is a live tissue. In some embodiments, the printhead comprises a needle, an extended cylinder, a fluid line, a print nozzle, or a plurality of print nozzles. In some embodiments, each print nozzle of the plurality of print nozzles is independently controlled and actuated. In some embodiments, each print nozzle of the plurality of print nozzles is actuated to eject an individual droplet of the bio-ink. In some embodiments, the plurality of print nozzles ejects the individual droplet simultaneously. In some embodiments, the plurality of print nozzles ejects the individual droplet in a specified sequence. In some embodiments, the printhead ejects the bio-ink continuously. In some embodiments, the bio-ink comprises a plurality of cells, a component of extracellular matrix, a synthetic polymer, a natural polymer, a cross-linking agent, a photoinitiator, or a combination thereof. In some embodiments, the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, and progenitors thereof. In some embodiments, the plurality of cells comprises chondrocytes. In some embodiments, the component of extracellular matrix comprises collagen, elastin, fibrillin, fibronectin, laminin, fibrinogen, tenascin, thrombospondin, integrin, hyaluronic acid, heparin, heparin sulfate, chondroitin sulfate, keratin sulfate, dermatan sulfate, or a combination thereof. In some embodiments, the synthetic polymer is polyethylene glycol (PEG), a PEG macromere, polyethylene glycol methacrylate (PEGMA), polyethylene dimethacrylate (PEDGMA), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide, or a combination thereof. In some embodiments, the natural polymer is alginate, cellulose, gelatin, pectin, agarose, chitosan, or a combination thereof. In some embodiments, the cross-linking agent comprises calcium chloride, calcium sulfate, calcium carbonate, calcium ($Ca^{2+}$), magnesium ($Mg^{2+}$), glutaraldehyde, genipin, nordihydroguaiaretic acid, tannin acid, procyanidins, glycosaminoglycan (GAG), 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), or a combination thereof. In some embodiments, the method comprises polymerizing the bio-ink. In some embodiments, polymerizing the bio-ink comprises cross-linking the bio-ink. In some embodiments, cross-linking the bio-ink comprises delivering the cross-linking agent by the printhead to the bio-ink. In some embodiments, cross-linking the bio-ink comprises applying UV light from a light source to the bio-ink. In some embodiments, cross-linking the bio-ink comprises applying heat to the bio-ink. In some embodiments, the bioprinter comprises a second printhead. In some embodiments, the method comprises positioning a second bioprinter comprising a printhead within proximity of or in contact with the chondral defect. In some embodiments, the method comprises ejecting a second bio-ink from the printhead of the second bioprinter onto the chondral defect to form a second bio-ink layer. In some embodiments, the method comprises controlling the bioprinter with a control system. In some embodiments, the control system comprises a computer system. In some embodiments, the control system comprises a robotic arm operatively connected to the computer system. In some embodiments, the robotic arm is coupled to a body part of the individual. In some embodiments, the robotic arm positions the bioprinter. In some embodiments, the bioprinter is moved along an X, Y, or Z axis, or a combination thereof. In some embodiments, the bioprinter is rotated around the X, Y, or Z axis, or a combination thereof. In some embodiments, the control system controls a bio-ink printing parameter. In some embodiments, the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof. In some embodiments, visualizing the chondral defect occurs before, during, or after ejecting the bio-ink. In some embodiments, visualizing the chondral defect comprises imaging the chondral defect. In some embodiments, the method comprises positioning an endoscope within proximity of the chondral defect. In some embodiments, the endoscope visualizes the chondral defect. In some embodiments, the chondral defect is selected from a damaged tissue, eroded tissue, diseased tissue or degenerated tissue. In some embodiments, the chondral defect is in a joint selected from a knee joint, a hip joint, an elbow joint, a shoulder joint, a wrist joint, a spine joint, a finger joint, an ankle joint, or a foot joint. In some embodiments, the chondral defect is in a knee joint. In some embodiments, the chondral defect is an osteochondral defect.

Disclosed herein, in certain embodiments, are biological composition delivery systems comprising an endoscope, at least one bioprinter comprising at least one printhead, and a control system that controls the at least one bioprinter; wherein the biological composition is a bio-ink comprising a plurality of cells. In some embodiments, the plurality of cells is a plurality of autologous cells, allogeneic cells, or a combination thereof. In some embodiments, the plurality of cells is a plurality of chondrogenic precursors. In some embodiments, the plurality of cells is a plurality of pancreatic cells. In some embodiments, the plurality of cells is a plurality of hepatic cells. In some embodiments, the plurality of cells is a plurality of neural cells. In some embodiments, the plurality of cells is a plurality of retinal cells. In some embodiments, the plurality of cells is a plurality of immunologic cells. In some embodiments, the plurality of cells is a plurality of renal cells. In some embodiments, the plurality of cells is a plurality of hematopoietic cells. In some embodiments, the plurality of cells is a plurality of adipose cells. In some embodiments, the plurality of cells is a plurality of fibroblastic cells. In some embodiments, the plurality of cells is a plurality of osteoblastic cells. In some embodiments, the plurality of cells is a plurality of muscle cells. In some embodiments, the plurality of cells is a plurality of epithelial cells. In some embodiments, the plurality of cells is a plurality of endothelial cells. In some embodiments, the biological composition delivery system comprise a three dimensional scanner. In some embodiments, the three dimensional scanner is configured to create a point cloud of an internal tissue defect, a bio-ink construct, or a combination thereof. In some embodiments, the point cloud is used to design the bio-ink construct that complements the shape of the internal tissue defect of a patient. In some embodiments, the at least one printhead comprises a needle, a print nozzle, or a combination thereof. In some embodiments, the biological composition delivery systems comprise a first bioprinter comprising a first printhead and a second bioprinter comprising a second printhead; wherein the first printhead ejects a first bio-ink and the second printhead ejects a second bio-ink. In some embodiments, the system is portable. In some embodiments, the control system comprises a robotic arm operatively connected to a computer system. In some embodiments, the robotic arm: 1) positions the bioprinter within proximity of or in contact with an internal tissue defect, and 2) has six degrees of freedom. In some embodiments, the control system comprises a second robotic arm operatively connected to a computer system, wherein the second robotic arm has six degrees of freedom. In some embodiments, the endoscope is configured to provide an image of the internal tissue defect; wherein the image is used to provide feedback regarding the structure of a bio-ink construct during a bio-printing process in real time. In some embodiments, the plurality of cells is selected from chondrocytes, mesenchymal stem cells (MSCs), MSC-like cells, human embryonic stem cells (hESCs), induced pluripotent stem cells (iPSCs), or a combination thereof. In some embodiments, the plurality of cells is a plurality of chondrocytes. In some embodiments, the plurality of cells is a plurality of mesenchymal stem cells (MSCs). In some embodiments, the plurality of cells is a plurality of human embryonic stem cells (hESCs). In some embodiments, the plurality of cells is a plurality of induced pluripotent stem cells (iPSCs). In some embodiments, the bio-ink comprises a component of extracellular matrix. In some embodiments, the bio-ink comprises polylactic acid, methacrylated collagen, or a combination thereof. In some embodiments, the bio-ink comprises collagen. In some embodiments, the bio-ink comprises a cross-linking agent, a photoinitiator, or a combination thereof.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIG. 1A illustrates a printhead with a linear array of converging print nozzles. FIG. 1B illustrates a printhead with a linear array of diverging print nozzles. FIG. 1C illustrates a printhead with a linear array of print nozzles, wherein the levels of the individual print nozzles are not all in the same plane. Shown here are print nozzles that are deeper in the center. FIG. 1D illustrates a printhead with a two dimensional array of converging print nozzles. FIG. 1E illustrates printhead with a two dimensional array of diverging print nozzles. FIG. 1F illustrates a two dimensional array of print nozzles, wherein the level of individual print nozzles are not all in the same plane.

FIG. 2A illustrates print nozzles evenly distributed in a rectangular shape. FIG. 2B illustrates print nozzles distributed with one or more masks (an empty space devoid of print nozzles). FIG. 2C illustrates print nozzles distributed in a star shape. FIG. 2D illustrates print nozzles distributed in an elliptical shape. FIG. 2E illustrates individual print nozzles of different sizes and diameters, distributed in various locations, as well as each print nozzle bioprinting a different bio-ink, different cell type, different molecules, bioactive factors, matrix components, and/or pharmacologic agent.

FIG. 5A illustrates a bioprinter which ejects bio-ink via ink-jet based printing, through a single nozzle.

FIG. 5B illustrates a bioprinter which ejects bio-ink via ink-jet based printing through a plurality of nozzles.

DETAILED DESCRIPTION OF THE INVENTION

Figure 1A:
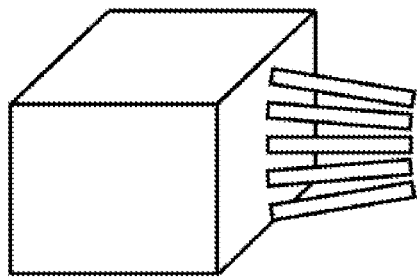
FIGS. 1A-1F illustrate different heights and angles of the print nozzles.

Bioprinting is the process of generating spatially-controlled cell patterns using three dimensional (3D) printing technologies, where cell function and viability are preserved within the printed construct. Bio-printing typically involves dispensing cells onto a biocompatible scaffold using a successive layer-by-layer approach to generate tissue-like three dimensional structures.

Surgical procedures can be performed with the systems disclosed herein in a minimally invasive manner. The benefits of minimally invasive surgery include less patient trauma, less blood loss, and faster recovery times when compared to traditional, open incision surgery. Furthermore, advantages of printing directly onto an internal tissue defect, as provided by the methods and systems disclosed herein, include, but are not limited to: i) eliminating the need for prior manufacturing, storage, or transportation; ii) providing the ability to customize the engineered tissue to perfectly fit defects of any shape or size; iii) eliminating the need to reconstruct, modify, or enlarge the defect to match the pre-engineered shape; iv) the ability to vary the type or amount of tissue being generated during surgery; v) the ability to combine artificial and natural scaffolds as well as living cells; and vi) enabling direct integration of the newly printed tissue into the host tissue.

Certain Terminology

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "about" or "approximately" means within an acceptable error range for the particular value as determined by one of ordinary skill in the art, which will depend in part on how the value is measured or determined, e.g., the limitations of the measurement system.

In certain embodiments, the term "about" or "approximately" means within 1, 2, 3, or 4 standard deviations. In certain embodiments, the term "about" or "approximately" means within 30%, 25%, 20%, 5%1, 10%, 9%, 8%, 7%, 6%, 5%, 4%, 3%, 2%, 1%, 0.5%, 0.1%, or 0.05% of a given value or range. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range.

As used herein, the terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

As used herein, the terms "user," "health care provider," or "surgeon" are used interchangeably and refer to the person or persons who will be operating the bioprinter and/or the bioprinting system.

As used herein, the terms "treating" or "treatment" of a state, disorder or condition (e.g., cancer) includes: (1) preventing or delaying the appearance of clinical or sub-clinical symptoms of the disorder developing in a human that is afflicted with or pre-disposed to the disorder but does not yet experience or display clinical or subclinical symptoms of the disorder; and/or (2) inhibiting the disorder, including arresting, reducing or delaying the clinical manifestation of the disorder or at least one clinical or sub-clinical symptom thereof; and/or (3) relieving the disorder, e.g., causing regression of the disorder or at least one of its clinical or sub-clinical symptoms; and/or (4) causing a decrease in the severity of one or more symptoms of the disorder. The benefit to a subject to be treated is either statistically significant or at least perceptible to the patient or to the physician.

As used herein, a "bio-ink" refers to a composition suitable for bioprinting comprising a biopolymer and/or a plurality of cells. In some embodiments, bio-ink comprises cell solutions, cell aggregates, cell-comprising gels, proteins, multicellular bodies, or tissues.

As used herein, "chondrocytes" includes chondrocytes, articular chondrocytes, fibrochondrocytes, chondroblasts, chondrocyte precursors, chondrocyte progenitors, mesenchymal stem cells, osteoblasts, immature chondrocytes, cartilage cells, chondrogenic cells, osteogenic cells, osteoprogenitor cells, osteochondroprogenitor cells, connective tissue fibroblasts, tendon fibroblasts, and cells that support the growth or differentiation of such cells.

As used herein, "polymerization" refers to both the process of forming a polymer chain and the process of forming networks of polymers. Polymerization includes cross-linking of polymers, including covalent and ionic cross-linking. In some embodiments, polymerization includes gelatinization, or gelling, of the bio-ink.

As used herein, the terms "chondrogenic precursor," "chondro-progenitor," "chondrocyte progenitor," "chondrocyte precursor" are used interchangeably.

As used herein, the term "embryonic stem cells" (ESCs) refers to pluripotent stem cells that are derived from a blastocyst before substantial differentiation of the cells into the three germ layers. ESCs include any commercially available or well established ESC cell line such as, by way of non-limiting example, H9, H1, H7, and SA002.

As used herein, the term "induced pluripotent stem cells" or "iPSCs" refers to somatic cells that have been reprogrammed into a pluripotent state resembling that of embryonic stem cells. Included in the definition of iPSCs are iPSCs of various types including human iPSCs and non-human iPSCs, such as iPSCs derived from somatic cells that are primate somatic cells or murine somatic cells.

As used herein, the term "allogeneic" means the plurality of cells are obtained from a genetically non-identical donor. For example, allogeneic cells are extracted from a donor and returned back to a different, genetically non-identical recipient.

As used herein, the term "autologous" means the plurality of cells are obtained from a genetically identical donor. For example, autologous cells are extracted from a patient and returned back to the same, genetically identical patient.

Methods of Bioprinting

Disclosed herein, in certain embodiments, are methods of bioprinting a bio-ink construct on an internal tissue defect during a minimally invasive surgery on an individual in need thereof, comprising: visualizing an internal tissue defect; positioning a bioprinter within proximity of or in contact with the internal tissue defect; and ejecting a bio-ink from the bioprinter onto the internal tissue defect to form a bio-ink layer, thereby generating a bio-ink construct.

Disclosed herein, in certain embodiments, are methods of bioprinting a bio-ink construct on a chondral defect during a minimally invasive surgery on an individual in need thereof, comprising: visualizing the chondral defect; positioning a bioprinter within proximity of or in contact with the chondral defect; and ejecting a bio-ink from the bioprinter onto the chondral defect to form a bio-ink layer, thereby generating a bio-ink construct.

In some embodiments, the methods of bioprinting comprise polymerizing the bio-ink. In some embodiments, polymerizing the bio-ink comprises applying a specified temperature or chemical to the bio-ink. In some embodiments, the method comprises polymerizing the bio-ink as it is printed on the substrate. In some embodiments, the method comprises photopolymerizing the bio-ink as it is printed on the substrate. In some embodiments, the method comprises polymerizing the bio-ink after it is printed on the substrate. In some embodiments, the method comprises photopolymerizing the bio-ink after it is printed on the substrate.

In some embodiments, the methods of bioprinting comprise gelling the bio-ink. In some embodiments, gelling the bio-ink comprises applying a specified temperature or chemical to the bio-ink. In some embodiments, the chemical is a cross-linking agent. In some embodiments, the bio-ink undergoes gelatinization. In some embodiments, gelatinization is induced by a change pH, a change in temperature, coulombic interactions, covalent bonding, non-covalent interactions, or polymerization.

In some embodiments, polymerizing the bio-ink comprises cross-linking the polymers in the bio-ink. In some embodiments, cross-linking the polymers in the bio-ink comprises chemical cross-linking. In some embodiments, cross-linking the polymers in the bio-ink occurs after the bio-ink is printed. In some embodiments, cross-linking the polymers in the bio-ink and printing occur simultaneously. In some embodiments, cross-linking the polymers in the bio-ink comprises cross-linking with a free radical initiator. In some embodiments, cross-linking the polymers in the bio-ink comprises crosslinking with thiol or amine moieties.

In some embodiments, cross-linking the polymers in the bio-ink comprises delivering a cross-linking agent to the bio-ink. In some embodiments, the cross-linking agent comprises calcium ($Ca^{2+}$), magnesium ($Mg^{2+}$), calcium chloride, calcium sulfate, calcium carbonate, glutaraldehyde, genipin, nordihydroguaiaretic acid, tannin acid, procyanidin, 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), or a combination thereof. In some embodiments, the cross-linking agent is delivered to the bio-ink by the bioprinter.

In some embodiments, the bio-ink turns into a solid during the printing process. In some embodiments, the method comprises polymerization or degradation of the bio-ink by exposure to electromagnetic radiation. In some embodiments the electromagnetic radiation comprises an electron beam, gamma-radiation, or UV radiation. In some embodiments, the method comprises polymerization or degradation of the bio-ink by exposure to light. In some embodiments, light is used to partially degrade a bioprinted tissue. In some embodiments, time, wavelength, and light intensity of light exposure are varied. In some embodiments, degradation or polymerization are paused by shuttering the light. In some embodiments, the gel continues polymerizing or degrading once light exposure resumes. In some embodiments, the method comprises adding a photoinitiator to the bio-ink. In some embodiments, any suitable photoinitiator is used. In some embodiments, the photoinitiator is a photoinitiator for UV curing. In some embodiments a type I photoinitiator or a type II photoinitiator is used. Examples of photoinitiators include, but are not limited to, Irgacure® 2959, 2-hydroxy-4'-(2-hydroxyethoxy)-2-methylpropiophenone, (2-hydroxy-1-[4-(2-hydroxyethoxy) phenyl]-2-methyl-1-propanone; lithium phenyl-2,4,6-trimethylbenzoylphosphinate (LAP); (2,2'-azobis[2-methyl-N-(2-hydroxyethyl)propionamide]; 2-isocyanotoethyl methacrylate; benzoyl benzylamine; camphorquinone; thiol-norbornene (thiol-ene); riboflavin; lucirin-TPO; Rose Bengal/furfuryl; ethyl eosin; methacrylic anhydride; 2,2-dimethoxy-2-phenylacetophenone; and Eosin Y. In some embodiments, the photoinitiator is added at a final concentration of about 0.01%, 0.02%, 0.03%, 0.04%, 0.05%, 0.1%, 0.15%, 0.2%, 0.25%, 0.3%, 0.35%, 0.4%, 0.45%, 0.5%, 0.6%, 0.7%, 0.8%, 0.9% or about 1% w/v gel. In some embodiments, the photoinitiator is added at a final concentration of about 0.05% w/v gel. In some embodiments, the method comprises removing bio-ink components (e.g. non-cellular components, non-ECM components) after bioprinting by physical, chemical, or enzymatic means. In some embodiments, the bio-ink components are removed by degradation of the bio-ink components.

In some embodiments, the method comprises bioprinting vascular cells. In some embodiments, bioprinting vascular cells results in formation of a blood vessel or a portion thereof. In some embodiments, the method of producing the bio-ink construct comprises bioprinting extracellular matrix components. In some embodiments, the method of producing the bio-ink construct comprises bioprinting vascular cells and extracellular matrix components. In some embodiments, bioprinting vascular cells and extracellular matrix comprises bioprinting endothelial cells, smooth muscle cells and fibrin. In some embodiments, the method comprises printing cartilage. In some embodiments, the method described herein comprises printing a pancreatic tissue. In some embodiments, the method described herein comprises printing a hepatic tissue. In some embodiments, the method described herein comprises printing a renal tissue. In some embodiments, the method described herein comprises printing a bladder or ureteral tissue. In some embodiments, the method described herein comprises printing a lung tissue. In some embodiments, the method described herein comprises printing vascular tissue. In some embodiments, the method described herein comprises printing retinal tissue. In some embodiments, the method described herein comprises printing neural tissue. In some embodiments, the method described herein comprises printing muscle tissue. In some embodiments, the method described herein comprises printing endothelial tissue. In some embodiments, the method described herein comprises printing epithelial tissue. In some embodiments, the method described herein comprises printing mucosal tissue. In some embodiments, the method described herein comprises printing fibrous tissue. In some embodiments, the method described herein comprises printing adipose tissue.

In some embodiments, the methods described herein comprise biomechanical testing of the bio-ink construct. In some embodiments, biomechanical testing tests the integrity of the bio-ink construct. In some embodiments, biomechanical testing comprises mechanical indentation, acoustic, ultrasonic analysis, or any suitable biomechanical testing technique.

In some embodiments, the methods described herein comprise bioprinting a bio-ink construct that has a structure or shape that is specific to a tissue defect of a patient. In some embodiments, the methods described herein comprise bioprinting a bio-ink construct that has a meniscal shape. In some embodiments, the methods described herein comprise bioprinting a bio-ink construct that has a structure or shape that complements the structure or shape of a tissue defect of a patient.

Visualizing the Defect

In some embodiments, the methods described herein comprise visualizing the internal tissue defect. In some embodiments, the visualizing the internal tissue defect comprises visualizing the internal tissue defect before, during, or after ejecting the bio-ink. In some embodiments, visualizing the internal tissue defect before ejecting the bio-ink is done pre-operatively. In some embodiments, pre-operative visualizing of the internal tissue defect comprises x-ray, CAT/CT scan, PET scan, MRI, ultrasound, thermography, endoscopy, or radiography of the internal tissue defect. In some embodiments, visualizing the internal tissue defect before ejecting the bio-ink is done during surgery, to generate an image of the to-be printed bio-ink construct. In some embodiments, visualizing the internal tissue defect is done in real-time during ejection of the bio-ink, in order to monitor the progress, fidelity, or accuracy of printing.

In some embodiments, visualizing the internal tissue defect comprises imaging the internal tissue defect before, during, or after ejecting the bio-ink. In some embodiments, imaging the internal tissue defect comprises generating an image of the internal tissue defect with a photograph, infrared imaging, three dimensional scanning, ultrasound, fluoroscopy, touch probing, or any suitable imagine technique.

In some embodiments, the image of the internal tissue defect is used to design a bio-ink construct. In some embodiments, the image of the internal tissue defect is used to determine the shape or structure of the bio-ink construct. In some embodiments, the image of the internal tissue defect is used to design a bio-ink construct that fits or aligns with a tissue defect of a patient. In some embodiments, the image of the internal tissue defect is used to design a bio-ink construct that is patient specific and matches the shape or construct of the tissue defect of the patient. In some embodiments, the image of the internal tissue defect is used to program a control system to execute the bio-ink printing parameter. In some embodiments, programming the control system is done manually. In some embodiments, programming the control system is done automatically. In some embodiments, the bio-ink printing parameter is altered. In some embodiments, the bio-ink printing parameter is altered by a healthcare provider. In some embodiments, the bio-ink printing parameter is altered during a surgical procedure.

In some embodiments, the methods comprise positioning an endoscope within proximity of the internal tissue defect. In some embodiments, the endoscope visualizes the internal tissue defect during bioprinting. In some embodiments, the endoscope is an arthroscope, bronchoscope, colonscope, colposcope, cystoeurethroscope, cystoscope, duodensocope, enteroscope, esophagogastroduodenscope, fetoscope, gastroscope, gynoscope, hysterscope, laparoscope, laryngoscope, peritoneoscope, proctosigmoidoscope, sigmoidoscope, thoracoscope, or ureteroscope. In some embodiments, the methods comprise positioning a second endoscope, a third endoscope, a fourth endoscope, or a fifth endoscope within proximity of the internal tissue defect.

Positioning the Bioprinter

In some embodiments, the methods described herein comprise positioning a bioprinter within proximity of or in contact with the internal tissue defect. In some embodiments, the method comprises positioning a second bioprinter within proximity of or in contact with the internal tissue defect. In some embodiments, the bioprinter is positioned within proximity of or in contact with the internal tissue defect by inserting the bioprinter into the patient through an incision in the skin of the patient. In some embodiments, the printhead is positioned within proximity of or in contact with the internal tissue defect by inserting the printhead into the patient through an incision in the skin of the patient. In some embodiments, the needle is positioned within proximity of or in contact with the internal tissue defect by inserting the needle into the patient through an incision in the skin of the patient. In some embodiments, the nozzle is positioned within proximity of or in contact with the internal tissue defect by inserting the nozzle into the patient through an incision in the skin of the patient. In some embodiments, a plurality of nozzles is positioned within proximity of or in contact with the internal tissue defect by inserting the plurality of nozzles into the patient through an incision in the skin of the patient.

Ejecting the Bio-Ink

In some embodiments, the methods described herein comprise bioprinting a bio-ink construct comprising a bio-ink composition. In some embodiments, the methods described herein comprise ejecting a bio-ink. In some embodiments, the printhead ejects bio-ink using an extrusion printing system. In some embodiments, the printhead ejects bio-ink using a droplet-based printing system. In some embodiments, the printhead ejects bio-ink using an ink-jet printing system.

Figure 3:
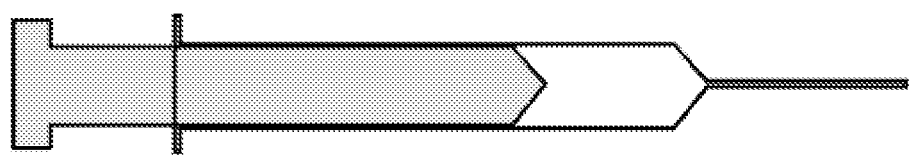
FIG. 3 illustrates a bioprinter which ejects bio-ink via syringe extrusion.

In some embodiments, the extrusion printing system comprises applying force, heat, or a combination thereof to eject the bio-ink. In some embodiments, the force is mechanical, pneumatic, or hydraulic force. In some embodiments, the extrusion printing system is a syringe (FIG. 3). In some embodiments, the syringe comprises a needle. In some embodiments, the extrusion printing system ejects the bio-ink continuously. In some embodiments, the extrusion printing system ejects the bio-ink continuously when the force or heat is applied. In some embodiments, the extrusion printing system ejects the bio-ink intermittently.

Figure 4:
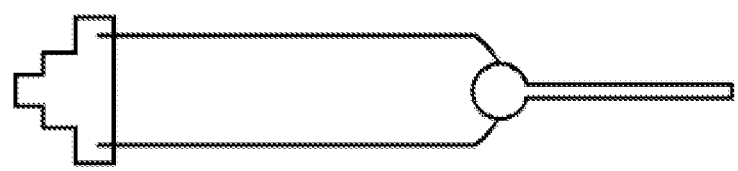
FIG. 4 illustrates a bioprinter which ejects bio-ink via diaphragm based jetting.

Ink-jet printing is a printing technique that reproduces digital pattern information onto a substrate with ink drops. In some embodiments, the ink-jet printing system is a thermal ink-jet system. In some embodiments, the ink jet printing system is a piezoelectric ink jet system. In some embodiments, the ink jet printing system uses mechanical vibration. In some embodiments, the extrusion printing system is a diaphragm-based jetting implement (FIG. 4). In some embodiments, the bioprinter of FIG. 4 is connected to an air supply source (not shown), which supplies pressurized air to the bioprinter. In some embodiments, the pressurized air directs a bio-ink from a reservoir containing the bio-ink to a nozzle, thereby creating a continuous stream of bio-ink. In some embodiments, a mechanical vibration interrupts the continuous stream of bio-ink and breaks up the stream of bio-ink into individual bio-ink droplets.

In some embodiments, the inkjet printing system comprises a heating element in each print nozzle. In some embodiments, the heating element raises the local print nozzle temperature to about 100° C., about 150° C., about 200° C., about 250° C., about 260° C., about 270° C., about 280° C., about 285° C., about 290° C., about 295° C., about 298° C., about 300° C., about 302° C., about 305° C., about 310° C., about 315° C., about 320° C., about 325° C., about 350° C., about 375° C., or about 400° C. In some embodiments, the heating element raises the local nozzle temperature to about 300° C. In some embodiments the heating element raises the temperature of the plurality of cells in the bio-ink about PC, about 2° C., about 3° C., about 4° C., about 5° C., about 6° C., about 7° C., about 8° C., about 9° C., about 10° C., about 11° C., about 12° C., about 13° C., about 14° C. or about 15° C. In some embodiments, the temperature of the plurality of cells in the bio-ink is raised for less than about 1 μsec, about 2 μsec, about 3 μsec, about 4 μsec, about 5 μsec, about 6 μsec, about 7 μsec, about 8 μsec, about 9 μsec or about 10 μsec. In some embodiments, the ink-jet printing system comprises one print nozzle. In other embodiments, the ink-jet printing system comprises a plurality of print nozzles.

Bio-Ink Compositions

Disclosed herein, in certain embodiments, are bio-ink compositions. In some embodiments, the bio-ink compositions are produced by the methods and systems disclosed herein. Bio-ink compositions disclosed herein may be in the form of a fluid, gel, or a construct. In some embodiments, the term "gel" as used herein refers to a soft, solid, or solid-like composition that exhibits reduced or no flow when in the steady state, and it is characterized by a high viscosity. In some embodiments, the gel is a mixture. In some embodiments, the gel comprises a fluid. In some embodiments, the gel comprises water. In some embodiments, the gel is a hydrogel, an aerogel, a nanocomposite hydrogel, a xerogel, an organogel, a synthetic gel, a natural gel, or a combination thereof. In some embodiments, a bio-ink composition is used in a method of treatment disclosed herein. In some embodiments, a bio-ink composition is used in a method of surgery of a human or an animal disclosed herein.

Bio-ink compositions disclosed herein may comprise a plurality of cells, a component of extracellular matrix, a growth factor, a therapeutic agent, a synthetic polymer, a natural polymer, a cross-linking agent, a photoinitiator, or a combination thereof. In some embodiments, the bio-ink comprises a plurality of cells. In some embodiments, the cell density of bio-ink is about 1 cell/pL, about 10 cells/pL, about 100 cells/pL, about 1 cell/nL, about 10 cells/nL, about 100 cells/nL, about 1 cell/µL, about 10 cells/µL, about 100 cells/µL, about 1000 cells/µL, about 10,000 cells cells/µL, about 100,000 cells/µL. In some embodiments, the cell density of the bio-ink is about $2\times10^6$ cells/mL, about $3\times10^6$ cells/mL, about $4\times10^6$ cells/mL, about $5\times10^6$ cells/mL, about $6\times10^6$ cells/mL, about $7\times10^6$ cells/mL, about $8\times10^6$ cells/mL, about $9\times10^6$ cells/mL, about $10\times10^6$ cells/mL, about $15\times10^6$ cells/mL, about $20\times10^6$ cells/mL, about $25\times10^6$ cells/mL, about $30\times10^6$ cells/mL, about $35\times10^6$ cells/mL, about $40\times10^6$ cells/mL, about $45\times10^6$ cells/mL, or about $50\times10^6$ cells/mL. In some embodiments, the plurality of cells comprises one cell type. In some embodiments, the plurality of cells comprises a combination of cell types. In some embodiments, the plurality of cells comprises more than one cell type. In some embodiments, the plurality of cells comprises about 2, about 3, about 4, about 5, about 6, about 7, about 8, about 9, about 10, about 12, about 14, about 16, about 18, about 20, about 25, about 30, about 35, about 40, about 45, about 50, about 55, about 60, about 65, about 70, about 75, about 80, about 85, about 90, about 95 or about 100 cell types. In some embodiments, the bio-ink comprises more than 100 cell types.

In some embodiments, the plurality of cells comprises chondrocytes, chondroprogenitor cells, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, vascular smooth muscle cells kidney cells, pancreatic cells, immune cells, stem cells, germ cells, nurse cells, interstitial cells, stellate cells liver cells, gastrointestinal cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblasts, Schwann cells, adipose cells, bone cells, bone marrow cells, cartilage cells, pericytes, mesothelial cells, cells derived from endocrine tissue, stromal cells, progenitor cells, lymph cells, endoderm-derived cells, ectoderm-derived cells, mesoderm-derived cells, pericytes, or progenitors thereof and/or a combination thereof. In some embodiments, the plurality of cells comprises chondrocytes. In some embodiments, the plurality of cells comprises chondroblasts. In some embodiments, the bio-ink composition comprises a plurality of chondrocytes. In some embodiments, the bio-ink composition comprises a plurality of mesenchymal stem cells. In some embodiments, the plurality of cells comprise connective tissue fibroblasts, tendon fibroblasts, bone marrow reticular tissue fibroblasts, non-epithelial fibroblasts, pericytes, osteoprogenitor cells, osteoblasts, or osteoclasts or any combination thereof. In some embodiments, the plurality of cells comprises articular chondrocytes. In some embodiments, the plurality of cells is selected from stem cells, progenitor cells, totipotent cells, pluripotent cells, induced pluripotent stem cells, undifferentiated cells, differentiated cells, differentiating cells, transdifferentiating cells, cells from an adult, cells from a child, germ cells, circulating cells, resident cells, adherent cells, malignant cells, tumor cells, proliferating cells, quiescent cells, senescent cells, apoptotic cells, cytokine-producing cells, migrating cells, or a combination thereof. In some embodiments, the bio-ink comprises a plurality of cells that express cell adhesion molecules. In some embodiments, cell adhesion molecules are selected from one or more of an adherin, a cadherin, a calsyntenin, a claudin, a cluster differentiation protein, a contactin, an immunoglobulin, an integrin, a lectin, a nectin, an occludin, a vinculin, a porimin, a podoplanin, a podocalyxin, a periostin, a neurotrimin, a neurexin, and a selectin. In some embodiments, the cell adhesion molecule is a receptor. In some embodiments, the cell adhesion molecule is a transmembrane protein.

In some embodiments, the plurality of cells comprises a genetic mutation. In some embodiments, the plurality of cells comprises a naturally-occurring genetic mutation. In some embodiments, the naturally-occurring genetic mutation is a germline genetic mutation or a somatic genetic mutation. In some embodiments, the plurality of cells comprises an induced genetic mutation. In some embodiments, the induced genetic mutation comprises a random genetic mutation or a targeted genetic mutation. In some embodiments, one or more genes in the plurality of cells comprise a genetic mutation. In some embodiments, 2, 3, 4, 5, 6, 7, 8, 9 or 10 genes in the plurality of cells comprise a genetic mutation. In some embodiments, more than 10 genes in the plurality of cells comprise a genetic mutation. In some embodiments, a gene comprises a plurality of genetic mutations. In some embodiments, the plurality of cells has been genetically modified. In some embodiments, the plurality of cells is transfected with a nucleic acid. In some embodiments, the cells have been infected by a virus comprising a nucleic acid. In some embodiments, the plurality of cells has been transduced by a virus comprising a nucleic acid. In some embodiments, the virus is selected from a retrovirus, adenovirus or adeno-associated virus. In some embodiments, the nucleic acid is selected from a vector, a plasmid, a gene, a non-coding nucleic acid, an exon, an intron, a double stranded DNA, a single stranded DNA, a RNA, a siRNA or a miRNA. In some embodiments, the nucleic acid is a gene. In some embodiments, the gene is a eukaryotic gene. In some embodiments, the gene is a prokaryotic gene. In some embodiments, the nucleic acid encodes a label or an affinity tag.

In some embodiments, the plurality of cells comprises one or more labels. In some embodiments, the one or more labels comprise a fluorescent probe. In some embodiments, the fluorescent probe is selected from a CellTrace™ or CellTracker™ (Life Technologies, Carlsbad, CA, USA). In some embodiments, the label comprises a fluorescent tag. In some embodiments, the fluorescent tag is mPlum, mCherry, tdTomato, mStrawberry, J-Red, DsRed-monomer, mOrange, mKO, mCitrine, Venus, YPet, EYFP, Emerald EGFP, CyPet, mCFPm, Cerulean, T-Sapphire, GFP or YFP. In some embodiments the plurality of cells comprises an affinity tag. In some embodiments, the affinity tag is a peptide. In some embodiments, the peptide is myc-tag, c-myc tag, FLAG-tag, His-tag, polyhistidine tag, HA-tag, V5, VSVG, softag 1, softag 3, express tag, S tag, fluorescein isothiocyanate (FITC), dinitrophenyl, trinitrophenyl, peridinin chlorophyll protein complex, biotin, phycoerythrin (PE), streptavidin, avidin, horse radish peroxidase (HRP), palmitoylation, nitrosylation, alkaline phosphatase, glucose oxidase, gluta-thione-S-transferase (GST), SUMO tag, thioredoxin, poly (NANP), poly-Arg, calmodulin binding protein, PurF fragment, ketosteroid isomerase, PaP3.30, TAF12 histone fold domain, maltose binding protein, or a fragment thereof. In some embodiments, the plurality of cells is from a tissue bank. In some embodiments, the plurality of cells is frozen or previously frozen. In some embodiments, the plurality of cells are harvested or isolated from a donor tissue. In some embodiments, the donor tissue is harvested from a live animal. In some embodiments, the donor tissue is derived from a monkey, an ape, a gorilla, a chimpanzee, a cow, a horse, a dog, a cat, a goat, a sheep, a pig, a rabbit, a chicken, a turkey, a guinea pig, a rat or a mouse. In some embodiments, the donor tissue is synthetic. In some embodiments, the plurality of cells is harvested from a live human donor. In some embodiments, the plurality of cells is derived from the individual. In some embodiments, the donor tissue is harvested from a cadaver. In some embodiments, the plurality of cells is harvested from a cadaver. In some embodiments, wherein the plurality of cells is harvested from a cadaver, the plurality of cells is harvested less than about 1 hour, less than about 2 hours, less than about 4 hours, less than about 6 hours, less than about 12 hours, less than about 24 hours, less than about 36 hours, less than about 48 hours, less than about 72 hours after death. In some embodiments, the plurality of cells is harvested from a cadaver less than about 72 hours after death. In some embodiments, the plurality of cells is harvested from a cadaver between 22 h and 72 h after death. In some embodiments, the plurality of cells is treated with an antibiotic and/or an antimycotic after or while they are isolated or harvested. In some embodiments, the antibiotic is penicillin, streptomycin, actinomycin D, ampicillin, blasticidin, carbenicillin, cefotaxime, fosmidomycin, gentamicin, kanamycin, neomycin, polymyxin B, or any combination thereof. In some embodiments, the antimycotic is amphotericin B, nystatin, natamycin or any combination thereof.

In some embodiments, the plurality of cells is propagated or maintained in a cell culture media after they are isolated and before they are bioprinted. In some embodiments, cell culture media comprises essential nutrients, growth factors, salts, minerals, vitamins, platelet-rich plasma, or a combination thereof. In some embodiments, particular ingredients are selected to enhance cell growth, differentiation or secretion of specific proteins. In some embodiments, cell culture media comprises cellular differentiation agents. In some embodiments, the plurality of cells is cultured with a supernatant or conditioned media from another population of cells in cell culture. In some embodiments, the plurality of cells are cultured in an atmosphere of about 1%, about 2%, about 3%, about 5%, about 7%, about 10% or about 20% $O_2$. In some embodiments, cells are cultured in an atmosphere of about 1%, about 2%, about 3%, about 4%, about 5%, about 6%, about 7%, about 8%, about 9% or about 10% $CO_2$. In some embodiments, cells are cultured at a temperature of about 30° C., about 32° C., about 33° C., about 34° C., about 35° C., about 36° C., about 37° C., about 38° C., about 39° C., about 40° C. or about 42° C. In some embodiments, human chondrocytes are preferably cultured at approximately 37° C. with humidified air containing 5% $CO_2$, media changed about every four days. In some embodiments, the plurality of cells are used for bioprinting when they grow to about 10%, about 20%, about 30%, about 40%, about 50%, about 60%, about 70%, about 80%, about 90%, about 100% confluence. In some embodiments the bio-ink is preferably maintained at a temperature of about 37° C. In some embodiments, the plurality of cells comprises human chondrocytes. In some embodiments, human chondrocytes are used for bioprinting when they grow to about 80% to 90% confluence. In some embodiments, the plurality of cells comprises chondrocytes, fibro-chondrocytes, or chondrogenic precursors. In some embodiments, the bio-ink composition comprises a plurality of chondrogenic precursors. In some embodiments, the bio-ink composition comprises a plurality of fibro-chondrocytes.

In some embodiments, the chondrocytes are derived from human embryonic stem cells (hESCs) (i.e. hESC-derived chondrocytes). In some embodiments, the bio-ink composition comprises a plurality of hESC-derived chondrocytes. In some embodiments, embryonic stem cells include any commercially available or well established ESC cell line such as H9, H1, H7, or SA002. In some embodiments, the chondrocytes are derived from non-human embryonic stem cells. In some embodiments, the chondrocytes are derived from induced pluripotent stem cells (iPSCs) (i.e. iPSC-derived chondrocytes). In some embodiments, the bio-ink composition comprises a plurality of iPSC-derived chondrocytes. In some embodiments, the chondrocytes are derived from mesenchymal stem cells (MSCs). In some embodiments, the bio-ink composition comprises a plurality of MSC-derived chondrocytes. In some embodiments, the chondrocytes are derived from mesenchymal stem cells (MSCs) that are not adult bone marrow MSCs. In some embodiments, the bio-ink composition comprises a plurality of chondrocytes derived from MSCs that are not bone marrow derived-MSCs. In some embodiments, the bio-ink composition comprises a plurality of chondrocytes derived from MSCs that are not adult bone marrow derived-MSCs. In some embodiments, chondrocytes are derived from hESC-derived mesenchymal stem cells (MSCs). In some embodiments, the bio-ink composition comprises a plurality of chondrocytes derived from hESC-derived MSCs. In some embodiments, chondrocytes are derived from H9 hESC-derived mesenchymal stem cells (MSCs). In some embodiments, the bio-ink composition comprises a plurality of chondrocytes derived from H9 hESC-derived MSCs. In some embodiments, chondrocytes are derived from H1 hESC-derived mesenchymal stem cells (MSCs). In some embodiments, the bio-ink composition comprises a plurality of chondrocytes derived from H1 hESC-derived MSCs. In some embodiments, chondrocytes are derived from H7 hESC-derived mesenchymal stem cells (MSCs). In some embodiments, the bio-ink composition comprises a plurality of chondrocytes derived from H7 hESC-derived MSCs. In some embodiments, chondrocytes are derived from SA002 hESC-derived mesenchymal stem cells (MSCs). In some embodiments, the bio-ink composition comprises a plurality of chondrocytes derived from SA002 hESC-derived MSCs. In some embodiments, chondrocytes are derived from iPSC-derived mesenchymal stem cells (MSCs). In some embodiments, the bio-ink composition comprises a plurality of chondrocytes derived from iPSC-derived MSCs.

In some embodiments, the chondrocytes are derived from MSC-like cells. In some embodiments, the bio-ink composition comprises a plurality of chondrocytes derived MSC-like cells. In some embodiments, MSC-like cells are defined as cells that express one or more markers selected from: CD44, CD151, SOX5, SOX6, and SOX9. In some embodiments, the population of MSC-like cells is at least 85% positive for CD73 and CD105. In some embodiments, the population of MSC-like cells is at least 95% positive for CD73. In some embodiments, the population of MSC-like cells is capable of multi-lineage differentiation into various tissues of mesenchymal origin. In some embodiments, the population of MSC-like cells is capable of differentiating into cells of adipogenic, osteogenic, chondrogenic, and myogenic lineages. In some embodiments, the population of MSC-like cells is capable of differentiating into adipocytes, chondrocytes, osteoblasts, and myocytes.

In some embodiments, the bio-ink composition comprises a plurality of chondrocytes derived from a plurality of chondrogenic precursors. In some embodiments, the bio-ink composition comprises a plurality of chondrogenic precursors. In some embodiments, the bio-ink composition comprises a mixture comprising a plurality of chondrocytes and a plurality of chondrogenic precursors. In some embodiments, the chondrogenic precursors express one or more markers selected from: aggrecan, Collagen II, collagen type 2A1, Collagen IV, and SOX9. In some embodiments, chondrogenic precursors are derived from stem cells (SCs). In some embodiments, chondrogenic precursors differentiate into chondrocytes. In some embodiments, chondrogenic precursors are capable of differentiating into chondrocytes only. In some embodiments, chondrogenic precursors are not capable of differentiating into a cell type that is not a chondrocyte. In some embodiments, chondrogenic precursors are not capable of differentiating into hypertrophic chondrocytes. In some embodiments, chondrogenic precursors do not differentiate into cells of adipogenic lineage, osteogenic lineage, myogenic lineages, or any combination thereof. In some embodiments, chondrogenic precursors do not differentiate into osteoblasts, osteocytes, osteoclasts, or any other type of bone cell. In some embodiments, chondrogenic precursors do not differentiate into adipocytes, monovacuolar cells, plurivacuolar cells, or any other type of fat cell. In some embodiments, chondrogenic precursors do not differentiate into myocytes, cardiomyocytes, skeletal myocytes, smooth muscle cells, or any other type of muscle cell.

In some embodiments, chondrogenic precursors are derived from pluripotent stem cells. In some embodiments, chondrogenic precursors are derived from human embryonic stem cells (hESCs). In some embodiments, chondrogenic precursors are derived from induced pluripotent stem cells (iPSCs). In some embodiments, chondrogenic precursors are derived from mesenchymal stem cells (MSCs). In some embodiments, chondrogenic precursors are derived from MSCs that are not adult bone marrow mesenchymal stem cells (MSCs). In some embodiments, chondrogenic precursors are derived from hESC-derived mesenchymal stem cells (MSCs). In some embodiments, chondrogenic precursors are derived from H9 hESC-derived mesenchymal stem cells (MSCs). In some embodiments, chondrogenic precursors are derived from H1 hESC-derived mesenchymal stem cells (MSCs). In some embodiments, chondrogenic precursors are derived from H7 hESC-derived mesenchymal stem cells (MSCs). In some embodiments, chondrogenic precursors are derived from SA002 hESC-derived mesenchymal stem cells (MSCs). In some embodiments, chondrogenic precursors are derived from iPSC-derived mesenchymal stem cells (MSCs). In some embodiments, the morphology of chondrogenic precursors is described as rounded or elongated with relatively lower cytoplasm to nuclear ratio.

In some embodiments, the chondrocytes or chondrogenic precursors are maintained in a cell culture comprising a growth factor. In some embodiments, the chondrocytes or chondrogenic precursors are maintained in a cell culture media comprising transforming growth factor-β3 (TGF-β3), basic fibroblast growth factor (bFGF), insulin-like growth factor-1 (IGF-1), bone morphogenetic factors (BMPs), platelet derived growth factors (PDGF), epidermal growth factor (EGF), or a combination thereof. In some embodiments, the chondrocytes or chondrogenic precursors are maintained in a cell culture media comprising BMP-1, BMP-2, BMP-3, BMP-4, BMP-5, BMP-6, BMP-7, BMP-8a, BMP-8b, BMP-10, BMP-15, or any combination thereof. In some embodiments, the chondrocytes or chondrogenic precursors are maintained in a cell culture media comprising PDGFA, PDGFB, PDGFC, PDGFD, PDGFRA, PDGFRB, or any combination thereof. In some embodiments, the chondrocytes or chondrogenic precursors are cultured in a three dimensional cell culture. In some embodiments, the three dimensional culture comprises a three dimensional matrix. In some embodiments, the three dimensional matrix is a gel matrix. In some embodiments, the gel matrix is Matrigel®. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, atelocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the three dimensional culture comprises pellet culture. In some embodiments, the chondrocytes or chondrogenic precursors are cultured condensed together, for example, as a packed or pelleted cell mass under gentle centrifugation.

In some embodiments, the bio-ink comprises a plurality of stem cells. In some embodiments, the bio-ink comprises a plurality of pluripotent stem cells. In some embodiments, the pluripotent stem cells are derived from chondrocytes. In some embodiments, the pluripotent stem cells are derived from autologous chondrocytes. In some embodiments, the pluripotent stem cells are derived from allogeneic chondrocytes. In some embodiments, the bio-ink comprises a plurality of embryonic stem cells. In some embodiments, the bio-ink comprises a plurality of human embryonic stem cells (hESCs). In some embodiments, the bio-ink comprises a plurality of non-human embryonic stem cells. In some embodiments, the bio-ink comprises a plurality of induced pluripotent stem cells (iPSCs). In some embodiments, the bio-ink comprises a plurality of MSCs. In some embodiments, the bio-ink comprises a plurality of MSCs, wherein the MSCs are not adult bone marrow MSCs. In some embodiments, the bio-ink comprises a plurality of MSCs, wherein the MSCs are derived from pluripotent stem cells. In some embodiments, the bio-ink comprises a plurality of MSCs, wherein the MSCs are derived from iPSCs. In some embodiments, the bio-ink comprises a plurality of MSCs, wherein the MSCs are derived from hESCs. In some embodiments, the bio-ink comprises a plurality of MSCs, wherein the MSCs are derived from H9 hESCs. In some embodiments, the bio-ink comprises a plurality of MSCs, wherein the MSCs are derived from H1 hESCs. In some embodiments, the bio-ink comprises a plurality of MSCs, wherein the MSCs are derived from H7 hESCs. In some embodiments, the bio-ink comprises a plurality of MSCs, wherein the MSCs are derived from SA002 hESCs. In some embodiments, the bio-ink comprises a plurality of MSCs, wherein the MSCs are derived from H1 hESCs. In some embodiments, the bio-ink comprises a plurality of MSC-like cells, as defined supra.

In some embodiments, the bio-ink comprises a cell culture medium. In some embodiments, cell culture media is selected from Balanced Salts, Dulbecco's Modified Eagle's Medium, Dulbecco's Modified Eagle's Medium/Nutrient F-12 Media, Ham's F-10 Media, Ham's F-12 Media, Minimum Essential Medium Eagle, Medium 199, RPMI-1640 Medium, Ames' Media, BGJb Medium (Fitton-Jackson Modification), Click's Medium, CMRL-1066 Medium, Fischer's Medium, Glasgow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium comprises a biological serum. In some embodiments, the serum is fetal bovine serum, fetal calf serum, fetal goat serum or horse serum. In some embodiments, the biological serum content of the cell culture medium is about 0.5% v/v, about 1% v/v, about 2% v/v, about 5% v/v, about 10% v/v, about 15% v/v, about 20% v/v, about 50% v/v, about 99% v/v, about 100% v/v. In some embodiments, the cell culture medium comprises a buffering agent. In some embodiments the buffering agent is selected from MES, ADA, PIPES, ACES, MOPSO, MOPS, BES, TES, HEPES, DIPSO, Acetamidoglycine, TAPSO, POPSO, HEPPSO, HEPPS, Tricine, Glycinamide, Bicine or TAPS.

In some embodiments, the bio-ink comprises a growth factor. In some embodiments, the growth factor is selected from Adrenomedullin (AM), Angiopoietin (Ang), Autocrine motility factor, Bone morphogenetic proteins (BMPs), Brain-derived neurotrophic factor (BDNF), Colony-stimulating factor (CSF), Epidermal growth factor (EGF), Erythropoietin (EPO), basic Fibroblast growth factor (bFGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), insulin, Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-β), Tumor necrosis factor-alpha (TNF-a), Vascular endothelial growth factor (VEGF), placental growth factor (P1GF), Fetal Bovine Somatotrophin (FBS), IL-1, IL-2, IL-3, IL-4, IL-5, IL-6, IL-7 or a combination thereof. In some embodiments, the bio-ink comprises TGF-β1 and bFGF.

In some embodiments, the bio-ink comprises a component of extracellular matrix. In some embodiments, the component of extracellular matrix comprises a structural protein, a specialized protein, a glycosaminoglycan (GAG), a proteoglycan, or a combination thereof. In some embodiments, a structural protein comprises collagen, elastin, and fibrillin. In some embodiments, the collagen comprises collagen type I, collagen type IL collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, collagen type XXIX or a combination thereof. In some embodiments, the specialized protein comprises fibronectin, laminin, fibrinogen, tenascin, thrombospondin, integrin, or a combination thereof. In some embodiments, the glycosaminoglycan comprises a repeating disaccharide unit. In some embodiments, the disaccharide unit comprises a modified sugar and hexuronic acid. In some embodiments, the modified sugar comprises N-acetylgalactosamine (GalNAc), N-acetylglucosamine (GlcNAc), or a combination thereof. In some embodiments, the hexuronic acid comprises glucuronate (GlcA) or iduronate (IdA). In some embodiments, the glycosaminoglycan comprises hyaluronic acid, dermatan sulfate, chondroitin sulfate, heparin, heparin sulfate, and keratin sulfate. In some embodiments, the glycosaminoglycan is linked to core proteins, forming a proteoglycan. In some embodiments, the core proteins are rich in serine (Ser) and threonine (Thr) residues. In some embodiments, the proteoglycan comprises a tetrasaccharide linker comprising a glucuronic acid (GlcA) residue, two galactose (Gal) residues, and a xylose (Xyl) residue. In some embodiments, the extracellular matrix is derived from a human, a cow, a horse, a sheep, a goat, a chimpanzee, a monkey, a rat, a pig, a mouse, a rabbit, or a synthetic reaction.

In some embodiments, the bio-ink comprises a synthetic polymer, a natural polymer, or a combination thereof. In some embodiments, the bio-ink is a gel. In some embodiments, the gel is a biogel or a hydrogel. In some embodiments, the synthetic polymer is polylactide (PLA), polycaprolactone (PCL), polyethylene glycol (PEG), a PEG macromer, polyethylene glycol methacrylate (PEGMA), polyethylene dimethacrylate (PEGDMA), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide or a combination thereof. In some embodiments, the gel comprises a PEGDMA hydrogel. In some embodiments, the PEGDMA polymer is 10% w/v hydrogel. In some embodiments, the PEGDMA polymer is 20% w/v hydrogel. In some embodiments, the gel does not comprise a synthetic polymer. In some embodiments, PEG macromers comprise reactive chain ends such as acrylate, methacrylate, allyl ether, maleimide, vinyl sulfone, N-hydroxysuccinimide (NHS) ester and vinyl ether groups. In some embodiments, the alcohol chain ends of PEG are esterified using acid chlorides (e.g., acryloyl chloride, methacryloyl chloride) in the presence of base. In some embodiments, PEG chain ends are etherified under basic conditions by reaction with alkyl halides such as 2-chloroethyl vinyl ether or allyl bromide. In some embodiments, acrylate, methacrylate, vinyl sulfone, maleimide, vinyl ether and allyl ether are capable of step growth network formation or polymerization. In some embodiments, polymerization of macromers is initiated using redox-generated radicals (e.g., ammonium persulfate and TEMED), or radicals generated with light. In some embodiments, the natural polymer is alginate, cellulose, gelatin, pectin, chitosan, paraffin, agarose, or a combination thereof. In some embodiments, the bio-ink comprises Matrigel®.

In some embodiments, the synthetic polymer or the natural polymer comprises a modification to enable crosslinking. In some embodiments, the modification to enable crosslinking is methacrylation. In some embodiments, the bio-ink comprises methacrylated collagen. In some embodiments, the bio-ink comprises methacrylated hyaluronic acid. In some embodiments, the bio-ink comprises a methacrylated extracellular matrix protein. In some embodiments, the synthetic polymer or the natural polymer comprises a functional molecule. In some embodiments, the functional molecule comprises a bioactive protein or drug. In some embodiments, the synthetic polymer or the natural polymer comprises a peptide to promote cell adhesion, a peptide to promote proliferation, or a peptide to promote differentiation. In some embodiments, the peptide to promote cell adhesion is arginyl-glycyl-aspartic acid (RGD). In some embodiments, the synthetic polymer or the natural polymer comprises a biodegradable link. In some embodiments, the biodegradable link is a matrix metalloproteinase (MMP)-sensitive link or an aggrecanase-sensitive link.

In some embodiments, the bio-ink comprises an additional agent. In some embodiments, the additional agent comprises a salicylic acid, a carboxylic acid, a lipid or fatty acid, a surfactant, a starch, a paraffin, a silica, a glycerol, or a combination thereof. In some embodiments, the lipid or fatty acid comprises palmitic acid, oleic acid, linolenic acid, omega-3 fatty acid or a combination thereof.

In some embodiments, the bio-ink comprises a biochemical factor. In some embodiments, the biochemical factor is selected from an anticoagulant, albumin, selenium, an amino acid, a vitamin, a hormone, a mineral, or any combination thereof. In some embodiments, the bio-ink comprises a protein. In some embodiments, the protein is a kinase, a hormone, a cytokine, a chemokine, an anti-inflammatory factor, a pro-inflammatory factor, an apoptotic factor or a steroid. In some embodiments, the bio-ink comprises an enzyme. In some embodiments, the enzyme is a protease, a collagenase, a nuclease, or a combination thereof. In some embodiments, the protease is a serine protease, a threonine protease, a cysteine protease, an aspartate protease, a glutamic acid protease, a metalloprotease, an exopeptidase, an endopeptidase, a trypsin, a chymotrypsin, a pepsin, a papain, an elastase, a carboxypeptidase, an aminopeptidase, a thrombase, a plasmin, a cathepsin, or snake venom.

In some embodiments, the bio-ink comprises a therapeutic agent. In some embodiments, the therapeutic agent is selected from an antibiotic and/or an antimycotic. In some embodiments, the antibiotic is penicillin, streptomycin, actinomycin D, ampicillin, blasticidin, carbenicillin, cefotaxime, fosmidomycin, gentamicin, kanamycin, neomycin, polymyxin B, or a combination thereof. In some embodiments, the antimycotic is amphotericin B, nystatin, natamycin or a combination thereof. In some embodiments, the therapeutic agent is selected from an anti-inflammatory therapeutic agent. In some embodiments, the anti-inflammatory therapeutic agent is a non-steroidal anti-inflammatory therapeutic agent. In some embodiments, the non-steroidal anti-inflammatory therapeutic agent is a cyclooxygenase (COX) inhibitor. In some embodiments, the COX inhibitor is selected from a COX1 inhibitor, COX2 inhibitor or combination thereof. In some embodiments, the anti-inflammatory therapeutic agent comprises a steroid. In some embodiments, the steroid is a glucocorticoid. In some embodiments, the glucocorticoid is dexamethasone.

In some embodiments, the method comprises positioning a light source within proximity of the internal tissue defect. In some embodiments, the light source is a laser. In some embodiments, the light source is a lamp. In some embodiments, the light source emits light in a focused region. In some embodiments, the light source emits light in a pattern. In some embodiments, the pattern of light cross-links the bio-ink. In some embodiments, the method comprises a wash step to remove the bio-ink which was not cross-linked. In some embodiments, the light source is connected to the endoscope. In some embodiments, the light source emits light with a visible wavelength of to 400 nm to 700 nm. In some embodiments, the light source emits UV light. In some embodiments, UV light comprises UV-A light, UV-B light, or UV-C light. In some embodiments, UV-A light comprises a wavelength of light between 315 nm and 400 nm. In some embodiments, UV-B light comprises a wavelength of light between 280 nm and 315 nm. In some embodiment, UV-C light comprises a wavelength of light between 100 nm to 280 nm. In some embodiments, the light source is an LED.

In some embodiments, the bio-ink is photopolymerizable. In some embodiments, the bio-ink is photodegradable. In some embodiments, the bio-ink comprises photo-releasable factors. In some embodiments, photo-releasable factors are selected from cells, growth factors, proteases, ligands, hormones, extracellular matrix, cytokines, anti-inflammatory factors, pro-inflammatory factors, adhesion molecules, or a combination thereof. In some embodiments, photo-releasable factors are used to form a feature of the bioprinted tissue (e.g. vasculature). In some embodiments, the bio-ink comprises a PEG with a degradable ester linkage. In some embodiments, the bio-ink comprises a factor that is attached to a component of the bio-ink or the extracellular matrix. In some embodiments, the factor is released by hydrolysis or enzymolysis of a bond that attaches the factor to the component of the gel or extracelluar matrix. In some embodiments, the factor is released by hydrolysis or enzymolysis of the gel component or the extracellular matrix. In some embodiments, the factor is released from the gel component or the extracellular matrix by the enzyme. In some embodiments, the enzyme is present in the internal tissue defect. In some embodiments, the factor released is a therapeutic agent or a growth factor. In some embodiments, the growth factor induces angiogenesis upon release.

Bio-Ink Constructs

Provided herein are bio-ink constructs, wherein the bio-ink constructs are produced by the methods and systems disclosed herein.

In some embodiments, the bio-ink construct comprises a plurality of bio-ink layers. In some embodiments, the bio-ink construct is a living tissue.

In some embodiments, the bio-ink construct has elevated glycosaminoglycan relative to respective cells in two dimensional cell culture and/or elevated proteoglycans relative to cells in two dimensional cell culture. In some embodiments, the average cell viability of the bio-ink construct is at least 60%, at least 65%, at least 70%, at least 75%, at least 80%, at least 85%, at least 90%, at least 95%, at least 98% or at least 99%. In some embodiments, the average cell viability of the bio-ink construct is about 90%. In some embodiments, the average cell viability of the bio-ink construct is about 100%.

In some embodiments, the bio-ink construct comprises a plurality of bio-ink layers. In some embodiments, each bio-ink layer comprises one or more cells. In some embodiments, a bio-ink layer comprises two or more cells. In some embodiments, a plurality of bio-ink layers is printed on to or in an internal tissue defect. In some embodiments, the internal tissue defect is in a human. In some embodiments, the internal tissue defect is in an animal. In some embodiments, the plurality of bio-ink layers is adjacent. In some embodiments, one or more cells of each bio-ink layer are adjacent to one or more cells of an adjacent bio-ink layer. In some embodiments, the bio-ink layers are the same dimension. In some embodiments, the bio-ink layers are each independently a suitable dimension. In some embodiments, the bio-ink construct comprises 2, 3, 4, 5, 6, 7, 8, 9, 10, 20, 30, 40, 50, 100 or more bio-ink layers. In some embodiments, the thickness of each layer of the plurality of bio-ink layers is independently about 10 µm, about 12 µm, about 14 µm, about 16 µm, about 18 µm, about 20 µm, about 30 µm, about 40 µm, about 50 µm, about 60 µm, about 70 µm, about 80 µm, about 90 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 500 µm, about 525 µm, about 550 µm, about 575 µm, about 600 µm, about 625 µm, about 650 µm, about 675 µm, about 700 µm, about 725 µm, about 750 µm, about 775 µm, about 800 µm, about 825 µm, about 850 µm, about 875 µm, about 900 µm, about 925 µm, about 950 µm, about 975 µm, or about 1 mm. In some embodiments the thickness of each layer of the plurality of bio-ink layers or live tissue of a construct is independently less than about 10 µm, less than about 12 µm, less than about 14 µm, less than about 16 µm, less than about 18 µm, less than about 20 µm, less than about 22 µm, less than about 24 µm, less than about 26 µm, less than about 28 µm or less than about 30 µm at its thinnest point.

In some embodiments, the bio-ink construct will be vascularized by surrounding tissue. In some embodiments, the bio-ink construct is avascular. In some embodiments, the bio-ink construct will not be vascularized by surrounding tissue. In some embodiments, the bio-ink construct comprises cartilage. In some embodiments, the bio-ink construct consists essentially of cartilage. In some embodiments, the water content of the cartilage is greater than about 20%, about 30%, about 40%, about 50%, about 60%, about 70%, about 72%, about 74%, about 75%, about 76%, about 77%, about 78%, about 79%, about 80%, about 81%, about 82%, about 83%, about 84%, about 85%, about 87%, or about 90%. In some embodiments, the water content of the cartilage is about 80%.

Bioprinting Systems

Provided herein are bioprinting systems for producing bio-ink constructs disclosed herein. Furthermore, these bioprinting systems may be used to perform methods of bioprinting disclosed herein. Bioprinting systems, as described throughout this instant application, may be used with various bio-ink compositions disclosed herein. In some embodiments, the systems described herein are biological composition delivery system. In some embodiments, the systems comprise a bioprinter, a control system, a display screen, a robotic arm, a light source, a sensor, an endoscope, a three dimensional scanner, or a combination thereof.

In some embodiments, the systems disclosed herein improve the accuracy and precision of placement and orientation of a surgical implant, bio-ink deposition, and bio-ink construct formation during surgery. In some embodiments, the system only prints in the desired area ensuring safer surgery. In some embodiments, the surgical implant is a bio-ink construct. In some embodiments, the surgical implant is a meniscal implant produced by the methods described herein. In some embodiments, the systems disclosed herein enable for adjustments during surgery involving tissue resection, deposition of a bio-ink, or positioning of a bio-ink construct. In some embodiments, the systems disclosed herein, when used during a surgery, improve recovery time of the patient after the surgery. In some embodiments, the systems disclosed herein, when used during a surgery, lower the amount of pain that the patient endures after the surgery.

Bioprinters

Figure 5A:
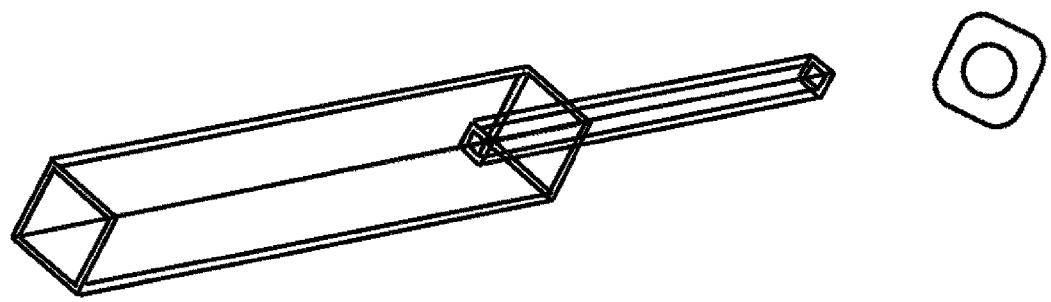
FIGS. 5A-5B illustrate a bioprinter which uses ink-jet based printing.
Figure 5B:
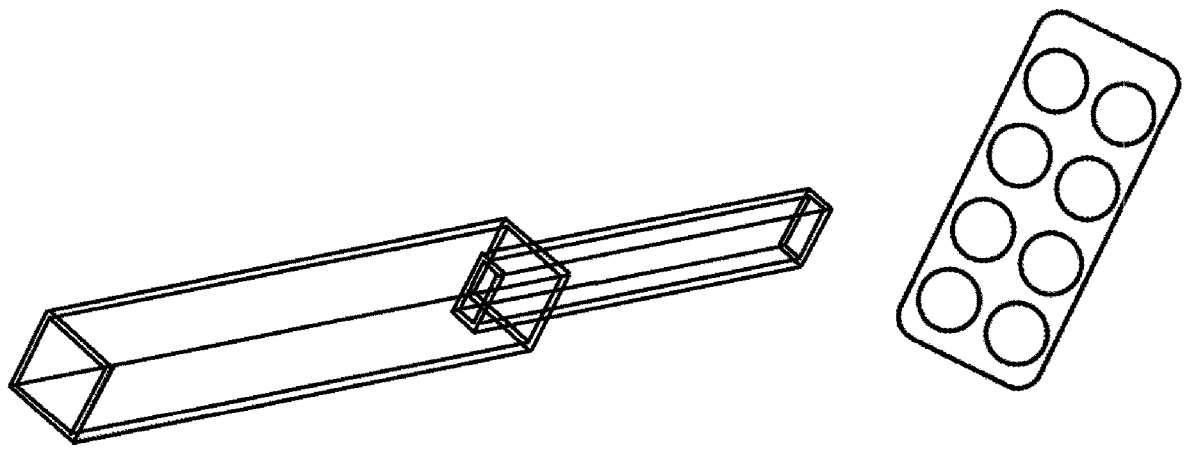

In some embodiments, the systems disclosed herein comprise a bioprinter. In some embodiments, the bioprinter comprises a printhead. In some embodiments, the printhead comprises a needle, an extended cylinder, a fluid line, a print nozzle (FIG. 5A), or a plurality of print nozzles (FIG. 5B). In some embodiments, the bioprinter comprises a second printhead. In some embodiments, the printhead is attached to a robotic arm. In some embodiments, a plurality of printheads is attached to a plurality of robotic arms. In some embodiments, the robotic arm guides the printhead. In some embodiments, the robotic arm guides the bioprinter. In some embodiments, the robotic arm positions the printhead within proximity of or in contact with the internal tissue defect. In some embodiments, the robotic arm positions the printhead within proximity of or in contact with the chondral defect. In some embodiments, the robotic arm positions the printhead within proximity of or in contact with curved or complex surfaces. In some embodiments, the robotic arm positions the bioprinter within proximity of or in contact with the internal tissue defect. In some embodiments, the robotic arm positions the bioprinter within proximity of or in contact with the chondral defect. In some embodiments, the robotic arm positions the bioprinter within proximity of or in contact with curved or complex surfaces.

In some embodiments, the size of the bioprinter enables the bioprinter to be inserted into the patient through an incision in the skin of the patient. In some embodiments, the size of the printhead enables the printhead to be inserted into the patient through an incision in the skin of the patient. In some embodiments, the diameter of the nozzle enables the nozzle to be inserted into the patient through an incision in the skin of the patient. In some embodiments, the diameters of a plurality of nozzles enable the plurality of nozzles to be inserted into the patient through an incision in the skin of the patient. In some embodiments, the diameter of the needle enables the needle to be inserted into the patient through an incision in the skin of the patient.

In some embodiments, the size of the bioprinter enables the bioprinter to be inserted into the patient through an incision in the skin of the patient during minimally invasive surgery, wherein the length of the incision is between about 1 mm and about 5 mm. In some embodiments, the size of the printhead enables the printhead to be inserted into the patient through an incision in the skin of the patient during minimally invasive surgery, wherein the length of the incision is between about 1 mm and about 5 mm. In some embodiments, the diameter of the needle enables the needle to be inserted into the patient through an incision in the skin of the patient during minimally invasive surgery, wherein the length of the incision is between about 1 mm and about 5 mm. In some embodiments, the diameter of the nozzle enables the nozzle to be inserted into the patient through an incision in the skin of the patient during minimally invasive surgery, wherein the length of the incision is between about 1 mm and about 5 mm. In some embodiments, the diameters of the plurality of nozzles enable the plurality of nozzles to be inserted into the patient through an incision in the skin of the patient during minimally invasive surgery, wherein the length of the incision is between about 1 mm and about 5 mm.

In some embodiments, the size of the bioprinter enables the bioprinter to be inserted into the patient through an incision in the skin of the patient. In some embodiments, the length of the incision in the skin of the patient ranges from about 1 mm to about 10 mm. In some embodiments, the length of the incision in the skin of the patient ranges from about 1 mm to about 5 mm. In some embodiments, the length of the incision in the skin of the patient ranges from about 5 mm to about 10 mm. In some embodiments, the length of the incision in the skin of the patient is about 1 mm. In some embodiments, the length of the incision in the skin of the patient is about 2 mm. In some embodiments, the length of the incision in the skin of the patient is about 3 mm. In some embodiments, the length of the incision in the skin of the patient is about 4 mm. In some embodiments, the length of the incision in the skin of the patient is about 5 mm. In some embodiments, the length of the incision in the skin of the patient is about 6 mm. In some embodiments, the length of the incision in the skin of the patient is about 7 mm. In some embodiments, the length of the incision in the skin of the patient is about 8 mm. In some embodiments, the length of the incision in the skin of the patient is about 9 mm. In some embodiments, the length of the incision in the skin of the patient is about 10 mm. In some embodiments, the length of the incision in the skin of the patient is between about 10 mm to about 50 mm. In some embodiments, the length of the incision in the skin of the patient is about 10 mm. In some embodiments, the length of the incision in the skin of the patient is about 20 mm. In some embodiments, the length of the incision in the skin of the patient is about 30 mm. In some embodiments, the length of the incision in the skin of the patient is about 40 mm. In some embodiments, the length of the incision in the skin of the patient is about 50 mm.

In some embodiments, the printhead comprises a plurality of print nozzles. In some embodiments, the plurality of print nozzles is arranged in an array. In some embodiments, the plurality of print nozzles is independently controlled and actuated. In some embodiments, the plurality of print nozzles is actuated to eject an individual droplet of the bio-ink. In some embodiments, the plurality of print nozzles ejects the individual droplet of bio-ink simultaneously. In some embodiments, the plurality of print nozzles ejects the individual droplet in a specified sequence. In some embodiments, the plurality of nozzles is arranged in a variety of configurations that have the ability to conform to curved and complex surfaces (FIGS. 1A-1F).

In some embodiments, the printhead stores the bio-ink. In some embodiments, the printhead stores 100 μp, 200 μl, 300 μl, 400 μl, 500 μp, 600 μl, 70 μl, 800 μl, 900 μl, 1 ml, 2 ml, 3 ml, 4 ml, 5 ml, 6 ml, 7 ml, 8 ml, 9 ml, 10 ml, 20 ml, 30 ml, 40 ml, 50 ml, 60 ml, 70 ml, 80 ml, 90 ml, 100 ml, 200 ml, 300 ml, 400 ml, or 500 ml of bio-ink. In some embodiments the printhead is disposable.

In some embodiments, the printhead comprises at least 5 print nozzles. In some embodiments, the printhead comprises about 6-20 print nozzles. In some embodiments, the printhead comprises 10, 12 or 16 print nozzles. In some embodiments, the printhead comprises about 5, about 10, about 15, about 20, about 25, about 30, about 35, about 40, about 45, about 50, about 55, about 60, about 65, about 70, about 75, about 80, about 85, about 90, about 95 or about 100 print nozzles. In some embodiments the diameter of the print nozzle is about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, or about 150 μm. In some embodiments, the diameter of the print nozzle is about 120 μm. In some embodiments, the diameter of the print nozzle is less than about 120 μm. In some embodiments, the diameter of the print nozzle is greater than 120 μm. In some embodiments, the printhead is a modified inkjet printhead. In some embodiments, the inkjet printhead is a thermal inkjet printhead. In some embodiments, the inkjet printhead is a piezoelectric inkjet printhead. In some embodiments, the printhead is a modified custom printhead. In some embodiments, the printhead is a custom printhead produced for bioprinting. In some embodiments, the printhead is a modified laser printhead.

In some embodiments, the print nozzles are arranged in one row of print nozzles. In some embodiments, the print nozzles are arranged in two rows of print nozzles. In some embodiments, the print nozzles are arranged in about 3, 4, 5, 6, 7, 8, 9, 10, 15, 20, 25, 30, 35, 40, 45, or 50 rows of print nozzles. In some embodiments, the print nozzles are arranged in two rows of 10, 12 or 16 print nozzles. In some embodiments, each row of print nozzles has the same number of print nozzles. In some embodiments, one or more rows of print nozzles have a different number of print nozzles from one or more other rows. In some embodiments, the length of the rows is described as the Y-axis of the row.

In some embodiments, the Y-axis spacing between print nozzles in a row of print nozzles is between about 5 micrometers and about 500 micrometers. In some embodiments, the Y-axis spacing between print nozzles in a row of print nozzles is between about 5 micrometers and about 200 micrometers, between about 5 micrometers and about 100 micrometers, between about 50 micrometers and about 200 micrometers, between about 1 micrometer and about 50 micrometers, or between about 200 micrometers and about 400 micrometers. In some embodiments, the Y-axis spacing between print nozzles in a row of print nozzles is between about 200 micrometers and about 400 micrometers. In some embodiments, the spacing between rows of print nozzles is between about 5 micrometers and about 500 micrometers. In some embodiments, the spacing between rows of print nozzles is between about 5 micrometers and about 200 micrometers, between about 5 micrometers and about 100 micrometers, between about 50 micrometers and about 200 micrometers, between about 1 micrometer and about 50 micrometers, or between about 200 micrometers and about 400 micrometers. In some embodiments, the spacing between rows of print nozzles is between about 200 micrometers and about 400 micrometers. In some embodiments of 10 print nozzles arranged in two rows, the Y-axis spacing between print nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi or about 300 dpi. In some embodiments of 10 print nozzles arranged in two rows, the Y-axis spacing between print nozzles is about 150 dpi. In some embodiments, the spacing between rows is about 200 μm, about 220 μm, about 240 μm, about 260 μm, about 280 μm, about 300 μm, about 320 μm, about 340 μm, about 360 μm, about 380 μm, about 400 μm, about 420 μm, about 450 μm, or about 500 μm. In some embodiments, the spacing between rows is about 340 μm. In some embodiments of 12 print nozzles arranged in two rows, the Y-axis spacing between print nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi or about 300 dpi. In some embodiments of 12 print nozzles arranged in two rows, the Y-axis spacing between print nozzles is about 180 dpi or 141 μm. In some embodiments, the spacing between rows is about 200 μm, about 220 μm, about 240 μm, about 260 μm, about 280 μm, about 300 μm, about 320 μm, about 340 μm, about 360 μm, about 380 μm, about 400 μm, about 420 μm, about 450 μm, or about 500 μm. In some embodiments, the spacing between rows is about 300 μm. In some embodiments of 16 print nozzles arranged in two rows, the Y-axis spacing between print nozzles is about 20 dpi, about 30 dpi, about 40 dpi, about 60 dpi, about 70 dpi, about 80 dpi, about 90 dpi, about 100 dpi, about 110 dpi, about 120 dpi, about 130 dpi, about 140 dpi, about 150 dpi, about 160 dpi, about 170 dpi, about 180 dpi, about 190 dpi, about 200 dpi, about 250 dpi, about 300 dpi, about 320 dpi, about 340 dpi, about 360 dpi, about 380 dpi, about 400 dpi, about 450 dpi or about 500 dpi. In some embodiments of 16 print nozzles arranged in two rows, the Y-axis spacing between print nozzles is about 300 dpi or 84 μm. In some embodiments, the spacing between rows is about 200 μm, about 220 μm, about 240 μm, about 260 μm, about 280 μm, about 300 μm, about 320 μm, about 340 μm, about 360 μm, about 380 μm, about 400 μm, about 420 µm, about 450 µm, or about 500 µm. In some embodiments, the spacing between rows is about 230 µm.

Figure 1B:
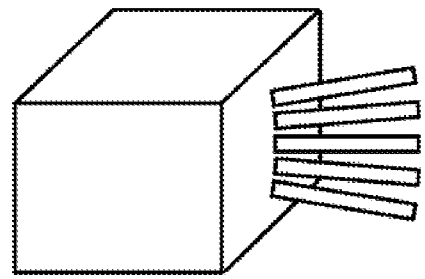
Figure 1C:
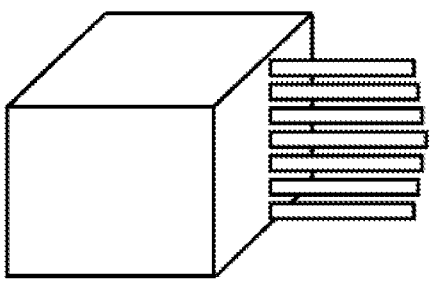
Figure 1D:
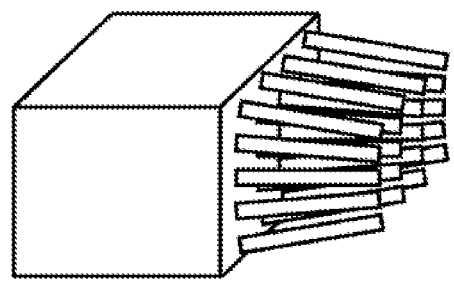
Figure 1E:
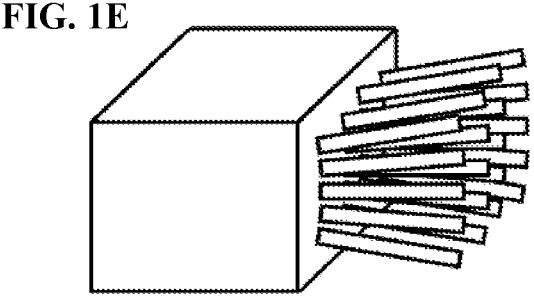
Figure 1F:
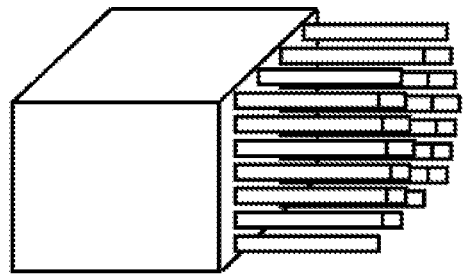

In some embodiments, the printhead comprises a configuration of print nozzles. In some embodiments, the configuration of print nozzles comprises parallel print nozzles. In some embodiments, the configuration comprises non-parallel print nozzles. In some embodiments, the configuration comprises converging print nozzles (FIGS. 1A and 1D). In some embodiments, the configuration comprises diverging print nozzles (FIGS. 1B and 1E). In some embodiments, the print nozzles are positioned at a level above or at the internal tissue defect. In some embodiments, the level is changed so as to increase or decrease proximity of the print nozzle to the internal tissue defect (FIGS. 1C and 1F). In some embodiments, the configuration comprises print nozzles with the level of the print nozzles all in the same plane (FIGS. 1C and 1F). In some embodiments, the configuration comprises print nozzles with the level of one or more print nozzles not in the same plane. In some embodiments, one or more configurations are combined. In some embodiments, the plurality of nozzles is arranged in a specific shape (FIGS. 2A-2E).

In some embodiments, the configuration of print nozzles comprises a print nozzle, wherein the direction of the print nozzle is modular. In some embodiments, the print nozzle permits drop volumes of bio-ink ejected from a printhead between about 2 picoliters and about 220 picoliters. In some embodiments, a bio-ink drop is about 1 pL, about 2 pL, about 5 pL, 10 pL, about 15 pL, about 20 pL, about 25 pL, about 30 pL, about 35 pL, about 40 pL, about 45 pL, about 50 pL, about 55 pL, about 60 pL about 65 pL, about 70 pL, about 75 pL, about 80 pL, about 85 pL, about 90 pL, about 95 pL, about 100 pL, about 105 pL, about 110 pL, about 115 pL, about 120 pL, about 125 pL, about 130 pL, about 135 pL, about 140 pL, about 145 pL, about 150 pL, about 155 pL, about 160 pL, about 165 pL, about 170 pL, about 175 pL, about 180 pL, about 185 pL, about 190 pL, about 195 pL, about 200 pL, about 250 pL, about 300 pL, about 500 pL, or about 1 nL. In some embodiments, the printhead has a resolution of at least about 100 dots per inch (dpi). In some embodiments, the printhead has a resolution of at least about 150 dpi, at least about 200 dpi, at least about 300 dpi, at least about 400 dpi, at least about 500 or more dpi, or about 1000 or more dpi. In some embodiments, the print nozzles fire with a frequency of about 1000 Hz, about 1200 Hz, about 1400 Hz, about 1600 Hz, about 1800 Hz, about 2000 Hz, about 2200 Hz, about 2400 Hz, about 2600 Hz, about 2800 Hz, about 3000 Hz, about 3200 Hz, about 3400 Hz, about 3600 Hz, about 3800 Hz, about 4000 Hz, about 4200 Hz, about 4400 Hz, about 4600 Hz, about 5000 Hz, about 5200 Hz, about 5400 Hz, about 5600 Hz, about 5800 Hz, or about 6000 Hz.

In some embodiments, the print nozzle is a coaxial nozzle. In some embodiments, the coaxial nozzle comprises two concentric nozzles comprising a first nozzle and a second nozzle. In some embodiments, the first nozzle is the inner nozzle and the second nozzle is the outer nozzle. In some embodiments, the first nozzle and the second nozzle eject a first bio-ink and a second bio-ink, respectively. In some embodiments, the first nozzle and the second nozzle eject bio-ink using different bio-ink printing parameters. In some embodiments, the coaxial nozzle comprises three concentric nozzles comprising a first nozzle, a second nozzle, and a third nozzle. In some embodiments, the first nozzle is the inner nozzle, the second nozzle is the middle nozzle, and the third nozzle is the outer nozzle. In some embodiments, the first nozzle, second nozzle, and third nozzle eject a first bio-ink, a second bio-ink, and a third bio-ink, respectively. In some embodiments, the first bio-ink, the second bio-ink, or the third bio-ink comprises the cross-linking agent. In some embodiments, the first bio-ink, the second bio-ink, or the third bio-ink comprises the synthetic polymer or the natural polymer. In some embodiments, the first bio-ink, the second bio-ink, or the third bio-ink comprises the plurality of cells. In some embodiments, the first nozzle, the second nozzle, and the third nozzle eject bio-ink using different bio-ink printing parameters. In some embodiments, the coaxial nozzle comprises four or more concentric nozzles. In some embodiments, the coaxial nozzle is used to create a vasculature in the bio-ink construct.

Figure 2A:
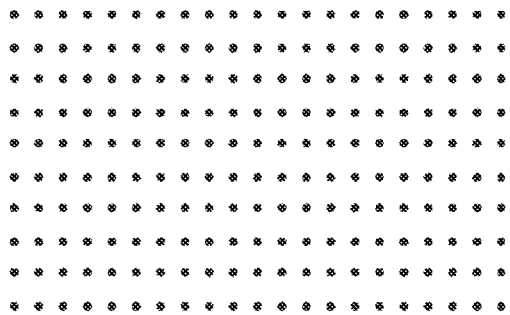
FIGS. 2A-2E illustrate different configures of print nozzles on a printhead.
Figure 2B:
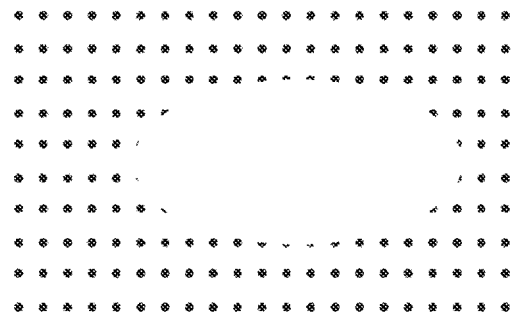
Figure 2C:
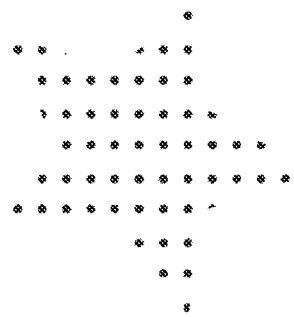
Figure 2D:
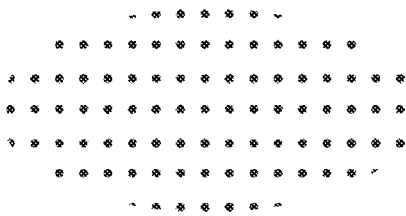
Figure 2E:
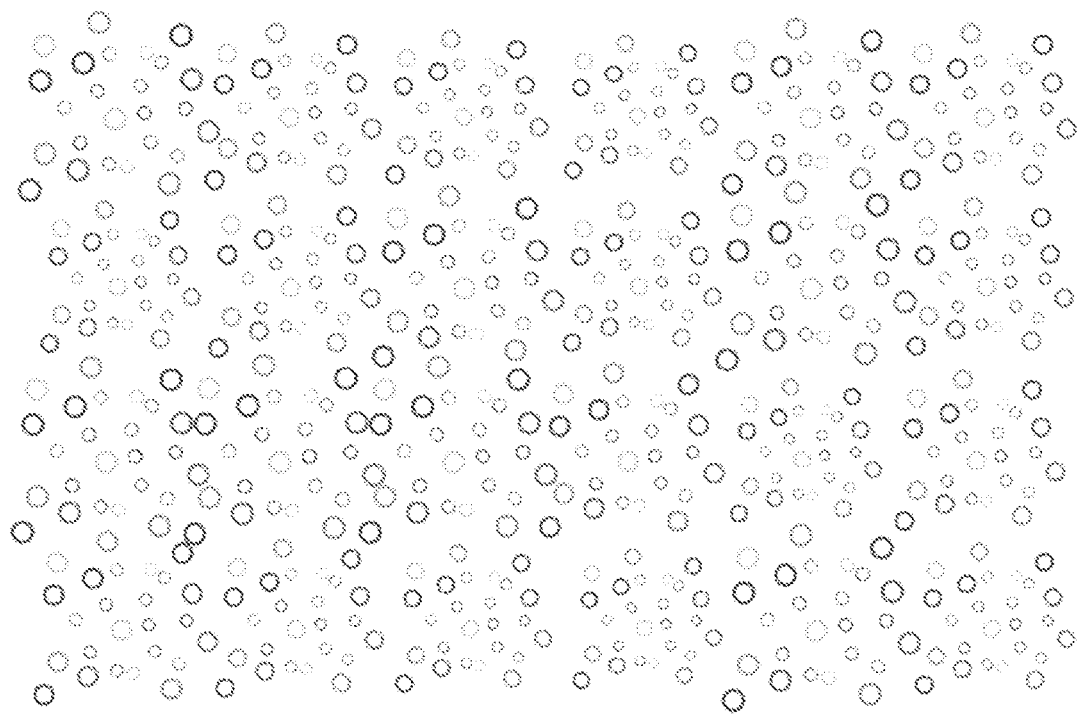

In some embodiments, the bioprinter comprises a plurality of printheads. In some embodiments, the plurality of printheads comprises a second printhead, a third printhead, a fourth printhead, a fifth printhead, a sixth printhead, a seventh printhead, an eight printhead, a ninth printhead, or a tenth printhead. In some embodiments, the plurality of print nozzles are of different sizes and diameters and are distributed in various locations (FIG. 2E). In some embodiments the plurality of print nozzles comprises coaxial nozzles, non-coaxial nozzles, or a combination thereof.

Control Systems

In some embodiments, the systems disclosed herein comprise a control system. In some embodiments, the control system is connected to the bioprinter. In some embodiments, the control system is in communication with the bioprinter. In some embodiments, the control system has wireless communication with the bioprinter. In some embodiments, the control system controls the bio-ink printing parameters of the bioprinter.

In some embodiments, the control system comprises a computer system. In some embodiments, the control system comprises a robotic arm operatively connected to the computer system. In some embodiments, the control system comprises a plurality of robotic arms operatively connected to the computer system. In some embodiments, the plurality of robotic arms comprises a second robotic arm, a third robotic arm, a fourth robotic arm, a fifth robotic arm, a sixth robotic arm, a seventh robotic arm, an eight robotic arm, a ninth robotic arm, or a tenth robotic arm. In some embodiments, the robotic arm is able to move in any direction and in any angle. In some embodiments, the robotic arm has six degrees of freedom. In some embodiments, the robotic arm has five degrees of freedom. In some embodiments, the robotic arm has four degrees of freedom. In some embodiments, the robotic arm has three degrees of freedom. In some embodiments, the robotic arm has two degrees of freedom. In some embodiments, the robotic arm enables the bioprinter to be positioned at any angle with respect to the substrate being printed on. In some embodiments, the increased flexibility in movement of the robotic arm enables the bioprinter to print directly onto a patient.

In some embodiments, the computer system comprises a computing device, a microcontroller, a processor, a memory device, an operating system, and a software module for monitoring or operating the printhead. In some embodiments, the computer system comprises a computing device. In some embodiments, the computing device is a microcontroller. In some embodiments, the microcontroller is an 8-bit, 16-bit, or 32-bit microcontroller. In some embodiments, the microcontroller is an 8051 microcontroller, a programmable interface controller (PIC), an AVR or Advanced Virtual RISC microcontroller, or an ARM® microcontroller.

In some embodiments, the computing device is a desktop computer or a laptop computer. In some embodiments, the computing device is a mobile device. In some embodiments, the mobile device is a smart phone or a smart watch. In some embodiments, the computing device is a portable device. In accordance with the description herein, suitable computing devices further include, by way of non-limiting examples, notebook computers, tablet computers, netbook computers, smart book computers, subnotebook computers, ultra-mobile PCs, handheld computers, personal digital assistants, Internet appliances, smart phones, music players, and portable video game systems. Many mobile smart phones are suitable for use in the systems described herein. Suitable tablet computers include those with booklet, slate, and convertible configurations. Suitable portable video game systems include, by way of non-limiting examples, Nintendo DS™ and Sony® PSP™.

In some embodiments, the computer system comprises a computer program including instructions executable by the processor causing the processor to: 1) control the movement and position of the robotic arm, 2) control a bio-ink printing parameter, and 3) control the bio-printing process. In some embodiments, the computer system controls the bio-printing process by directing the bioprinter to the location on the substrate where the bio-ink gets deposited.

In some embodiments, the computer system comprises a processor, a memory device, an operating system, and a software module for monitoring or operating the printhead. In some embodiments, the computer system comprises a digital processing device and includes one or more hardware central processing units (CPU). In further embodiments, the computer system includes an operating system configured to perform executable instructions. In some embodiments, the operating system is software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion@BlackBerry OS@, Google® AndroidR, Microsoft® Windows Phone@OS, Microsoft® Windows Mobile® OS, Linux, and Palm® WebOS. In some embodiments, the computer system includes a storage and/or memory device. In some embodiments, the storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM).

In some embodiments, the device is a storage device including, by way of non-limiting examples, CD-ROMs, DVDs, flash memory devices, magnetic disk drives, magnetic tapes drives, optical disk drives, and cloud computing based storage. In some embodiments, the storage and/or memory device is a combination of devices such as those disclosed herein.

In some embodiments, the computer systems described herein include user interfaces. In some embodiments, the input device is a keyboard. In further embodiments, the input device is a key pad. In a particular embodiment, the input device is a simplified key pad for use by a subject with communications limitations (e.g., due to age, infirmity, disability, etc.), wherein each key is associated with a color, a shape, and health/communication concept. In some embodiments, the input device is a pointing device including, by way of non-limiting examples, a mouse, trackball, track pad, joystick, game controller, or stylus. In some embodiments, the input device is the display screen, which is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein. In some embodiments, the systems, and software modules disclosed herein are intranet-based. In some embodiments, the systems and software modules are Internet-based. In some embodiments, the computer system comprises WiFi or Bluetooth interfaces. In further embodiments, the computer systems and software modules are World Wide Web-based. In still further embodiments, the computer systems and software modules are cloud computing-based. In other embodiments, the computer systems and software modules are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

Figure 6:
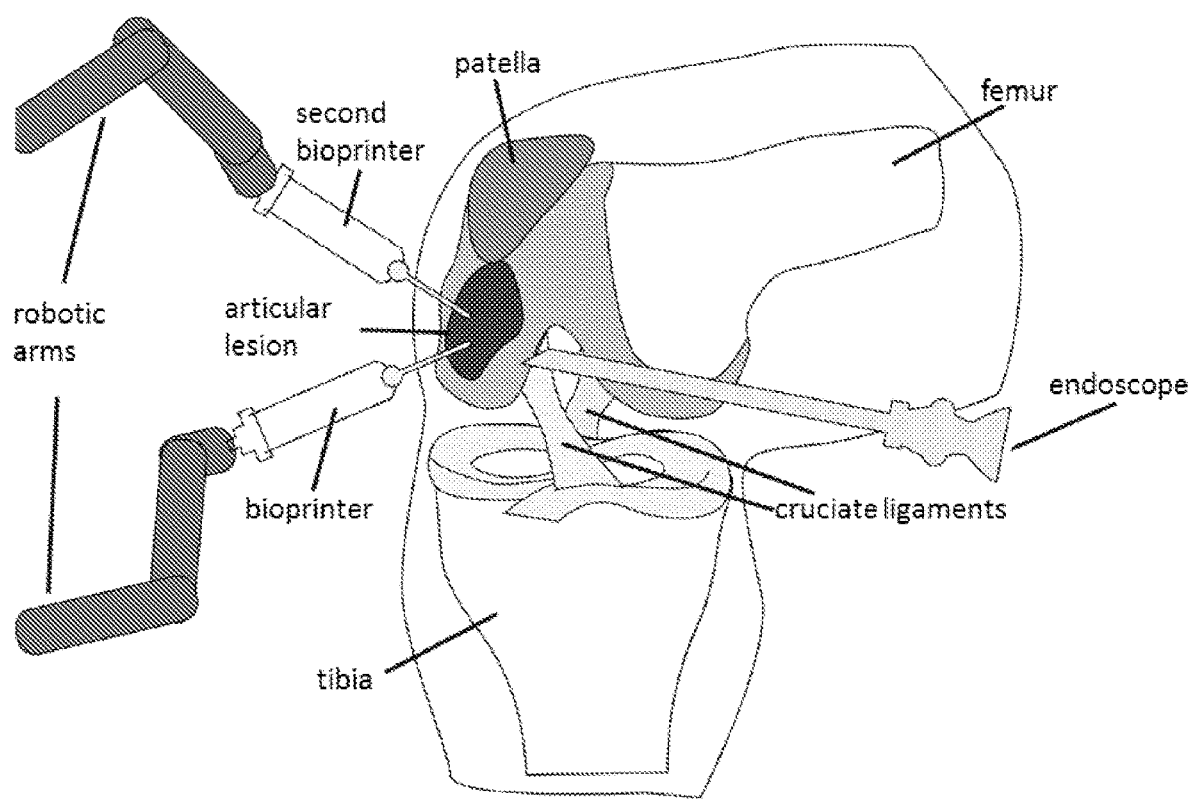
FIG. 6 exemplifies repair of an articular lesion in the knee using two bioprinters to print bio-ink, controlled by two robotic arms, and an endoscope to visualize the internal tissue defect.

In some embodiments, controls systems disclosed herein comprise a robotic arm operably connected to the computer system. In some embodiments, the robotic arm controls a position of the first bioprinter. In some embodiments the robotic arm moves the bioprinter along an X, Y, or Z axis, or a combination thereof. In some embodiments, the robotic arm rotates the bioprinter around the X, Y, or Z axis, or a combination hereof. In some embodiments, the robotic arm comprises part of a robotic surgical system. In some embodiments, the robotic surgical system is a Mako robotic surgical system. In some embodiments, the robotic arm is coupled to a body part. In some embodiments, the body part is the body part with the internal tissue defect. Coupling to a body part allows the control system to move with the body part should the body part be repositioned. In some embodiments, the control system comprises a second robotic arm operatively connected to the computer system. In some embodiments, the robotic arm controls a position of the second bioprinter (FIG. 6).

In some embodiments, the control system is configured to control a bio-ink printing parameter. In some embodiments the bio-ink printing parameter comprises temperature, backpressure, drops per nozzle, frequency of drop rate, number of nozzles in use, firing energy, resolution, viscosity, cell concentration, physiological temperature, speed of printing, or a combination thereof.

In some embodiments, the systems disclosed herein are capable of bioprinting a bio-ink construct on an internal tissue defect during a minimally invasive surgery on an individual in need thereof. The systems may comprise a control system, an endoscope, a display screen, a sensor, a light source, a 3D scanner, a robotic arm, and a bioprinter comprising a printhead.

In some embodiments, the systems disclosed herein are portable. In some embodiments, the systems are configured to be moved in and out of an operating room. By way of non-limiting example, the system may be mounted on wheels or a cart. Also by way of non-limiting example, the system may be small and light enough to be carried by hand of an average user.

In some embodiments, systems disclosed herein do not require the services of a live healthcare provider. For example, in some embodiments, the control systems described herein include a non-communication mode. In further embodiments, the methods described herein are operated in a non-communication mode when communication protocols fail, when communication channels or signals fail or are lost, or when devices are placed in a location where one or more communication protocols, channels, or signals are unavailable. In a non-communication mode, a live, remote healthcare provider is unable to monitor, supervise, or operate components of the system. By way of further example, in some embodiments, control systems described herein include an emergency mode. In an emergency mode, in some embodiments, components of a system act autonomously, without monitoring, supervision, or operation by a live or remote healthcare provider.

In some embodiments, the systems are programmable. In some embodiments, the control system is programmable. In some embodiments, the computer system is programmable. In some embodiments, the control system is programmable with information about an internal tissue defect or a subject to be treated using the system. Non-limiting examples of information about the internal tissue defect are shape, size dimension, thickness, density or proximity of the internal tissue defect.

In some embodiments, a healthcare provider programs information about the internal tissue defect into the computer system. In some embodiments, a healthcare provider inputs information about the internal tissue defect into the computer. In some embodiments, the information about the internal tissue defect comprises shape, size dimension, thickness, density or proximity of the internal tissue defect. In some embodiments, the, systems disclosed herein are employed, in part or in whole, in healthcare facilities such as hospitals, hospice, nursing homes, urgent care offices, diagnostic laboratories, and the like. In some embodiments, the systems are employed, in part or in whole, in veterinary facilities such as animal hospitals, veterinary offices, and the like.

In some embodiments, the control system comprises controlling a bio-ink printing parameter. In some embodiments the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof.

Display Screens

In some embodiments, the systems disclosed herein comprise a display screen. In some embodiments, the system for bioprinting a bio-ink construct comprises a plurality of display screens. In some embodiments, the display screen is operatively connected to the computer system. In some embodiments, the system for bioprinting a bio-ink construct comprises a connection to a display screen. In some embodiments, the display screen displays an image generated by an endoscope. In some embodiments, the display screen displays an image of an internal structure of a joint. In some embodiments, the display screen displays an image of an internal structure of a joint of a patient undergoing minimally invasive surgery. In some embodiments, the display screen displays an image on an internal structure of a knee of a patient undergoing minimally invasive surgery. In some embodiments, the display screen displays an image of a bio-construct printed by the bioprinter. In some embodiments, the display screen displays an image of a bio-construct printed by the bioprinter during minimally invasive surgery. In some embodiments, the display screen displays a real time image of a bio-construct being printed by the bioprinter. In some embodiments, the display screen displays a real time image of a bio-construct being printed by the bioprinter during minimally invasive surgery. In some embodiments, the display screen provides visual feedback of the bioprinting process. In some embodiments, the display screen provides visual feedback of the structural accuracy of the bio-construct during the bioprinting process and after the bioprinter process. In some embodiments, the display screen provides real time visual feedback of the location of the bio-construct being bioprinted by the bioprinter.

In some embodiments, the computer systems described herein include user interfaces. In further embodiments, the user interfaces include graphic user interfaces (GUIs). In still further embodiments, the user interfaces are interactive and present a user with menus and options for interacting with the computer systems and bioprinters described herein. In further embodiments, the computer system includes a display screen to send visual information to a user. In some embodiments, the display is a cathode ray tube (CRT). In some embodiments, the display screen is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In some embodiments, the display screen is a mobile device screen, a computer screen, a portable device screen, a touch screen, or a multi-touch screen. In still further embodiments, the display is a combination of displays such as those disclosed herein.

Robotic Arms

In some embodiments, the systems disclosed herein comprise at least one robotic arm. In some embodiments, the controls system comprises a robotic arm operatively connected to the computer system. In some embodiments, the control system comprises a second robotic arm operatively connected to the computer system. In some embodiments, the control system controls the robotic arm. In some embodiments, the robotic arm controls a position of the second bioprinter (FIG. 6). In some embodiments, the printhead is attached distally, with respect to the user (i.e. a surgeon), to a robotic arm. In some embodiments, a plurality of printheads is attached distally, with respect to the user (i.e. a surgeon), to a plurality of robotic arms. In some embodiments, the printhead is mounted to the distal end, with respect to the user, of a robotic arm. In some embodiments, a plurality of printheads is mounted to a distal end of a plurality of robotic arms. In some embodiments, the user is able to manually change or control the depth at which the printhead, which is attached to a robotic arm, is inserted into a patient during surgery. In some embodiments, the control system automatically controls the depth at which the printhead, which is attached to a robotic arm, is inserted into a patient during surgery. In some embodiments, the distal end of the robotic arm is the end portion of the robotic arm that is closest to the patient.

In some embodiments, a system comprising a plurality of robotic arms decreases surgery time. In some embodiments, a system comprises a plurality of robotic arms in which one or more arms control one or more printheads, while one or more arms control an imaging or a visualization device component or one or more sensors. In some embodiments, a system comprising a plurality of printheads decreases surgery time. In some embodiments, a system comprising a plurality of bioprinters decreases surgery time. In some embodiments, a system comprising a plurality of robotic arms enables more than one bio-ink to be deposited. In some embodiments, a system comprising a plurality of printheads enables more than one bio-ink to be deposited. In some embodiments, a system comprising a plurality of bioprinters enables more than one bio-ink to be deposited. In some embodiments, a system comprising a plurality of robotic arms enables a bio-ink construct comprising more than one bio-ink compositions to be bioprinted. In some embodiments, a system comprising a plurality of printheads enables a bio-ink construct comprising more than one bio-ink compositions to be bioprinted. In some embodiments, a system comprising a plurality of bioprinters enables a bio-ink construct comprising more than one bio-ink compositions to be bioprinted.

In some embodiments, the robotic arm comprises a base. In some embodiments, the base rotates 360 degrees. In some embodiments, the robotic arm extends from a base. In some embodiments, the robotic arm comprises a joint. In some embodiments, the robotic arm comprises a plurality of joints. In some embodiments, the robotic arm comprises one joint. In some embodiments, the robotic arm comprises two joints. In some embodiments, the robotic arm comprises three joints. In some embodiments, the robotic arm comprises four joints. In some embodiments, the robotic arm comprises five joints. In some embodiments, the robotic arm comprises six joints. In some embodiments, the plurality of joints allows the robotic arm to be rotated about six axes. In some embodiments, the plurality of joints allows the robotic arm to be rotated about five axes. In some embodiments, the plurality of joints allows the robotic arm to be rotated about four axes. In some embodiments, the plurality of joints allows the robotic arm to be rotated about three axes. In some embodiments, the robotic arm is manually rotated by the surgeon. In some embodiments, the robotic arm is automatically rotated by the control system.

In some embodiments, the robotic arm comprises an actuator. In some embodiments, the actuator is a rotational actuator. In some embodiments, the actuator is an electrical actuator. In some embodiments, the actuator is a direct current (DC) linear actuator. In some embodiments, the actuator is powered by a motor. In some embodiments, the robotic arm comprises a motor or a plurality of motors that power movement of the robotic arm. In some embodiments, the motor is an alternating current (A/C) motor, a direct current (DC) motor, a geared DC motor, an RC servo motor, a stepper motor, or an industrial servo motor. In some embodiments, the motor is controlled by a motor controller. In some embodiments, the motor controller is a brushed DC motor controller, a brushless DC motor controller, a servo motor controller, or a stepper motor controller. In some embodiments, the motor controller is operatively connected to the control system. In some embodiments, the robotic arm is controlled by the control system. In some embodiments, the motor controller is operatively connected to the computing system. In some embodiments, the robotic arm is controlled by the computing system. In some embodiments, the motor controller is operatively connected to the computing device. In some embodiments, the robotic arm is controlled by the computing device. In some embodiments, the motor controller is operatively connected to the microcontroller. In some embodiments, the robotic arm is controlled by the microcontroller. In some embodiments, the robotic arm is manually controlled. In some embodiments, the robotic arm is controlled by user. In some embodiments, the user is able to manually control the robotic arm at any time during a surgery. In some embodiments, the user is able to manually change or control the position of the robotic arm at any time during a surgery.

In some embodiments, the robotic arm controls a position of the bioprinter. In some embodiments the robotic arm moves the bioprinter along an X, Y, or Z axis, or a combination thereof. In some embodiments, the robotic arm rotates the bioprinter around the X, Y, or Z axis, or a combination hereof. In some embodiments, the robotic arm is able to move in any direction and in any angle. In some embodiments, the robotic arm has six degrees of freedom. In some embodiments, the robotic arm has five degrees of freedom. In some embodiments, the robotic arm has four degrees of freedom. In some embodiments, the robotic arm has three degrees of freedom. In some embodiments, the robotic arm has two degrees of freedom. In some embodiments, the robotic arm has one degree of freedom. In some embodiments, the robotic arm positions the printhead within proximity of or in contact with curved or complex surfaces. In some embodiments, the robotic arm positions the printhead within proximity of or in contact with the internal tissue defect. In some embodiments, the robotic arm positions the printhead within proximity of or in contact with the chondral defect.

In some embodiments, the robotic arm enables the bioprinter to be positioned at any angle with respect to the substrate being printed on. In some embodiments, the increased flexibility in movement of the robotic arm enables the bioprinter to print directly onto a tissue defect of a patient. In some embodiments, the robotic arm comprises part of a robotic surgical system. In some embodiments, the robotic surgical system is a Mako robotic surgical system. In some embodiments, the robotic arm is coupled to a body part. In some embodiments, the body part is the body part with the internal tissue defect. Coupling to a body part allows the control system to move with the body part should the body part be repositioned.

Light Sources

In some embodiments, the systems disclosed herein comprise a light source. In some embodiments, the light source is positioned within proximity of the internal tissue defect. In some embodiments, the light source is a laser. In some embodiments, the light source is a lamp. In some embodiments, the light source emits light in a focused region. In some embodiments, the light source emits light in a pattern. In some embodiments, the pattern of light cross-links the bio-ink. In some embodiments, the light source polymerizes the bio-ink. In some embodiments, the method comprises a wash step to remove the bio-ink which was not cross-linked. In some embodiments, the light source is connected to the endoscope. In some embodiments, the light source emits UV light. In some embodiments, UV light comprises UV-A light, UV-B light, or UV-C light. In some embodiments, UV-A light comprises a wavelength of light between about 315 nm and about 400 nm. In some embodiments, UV-B light comprises a wavelength of light between about 280 nm and about 315 nm. In some embodiment, UV-C light comprises a wavelength of light between about 100 nm to about 280 nm. In some embodiments, the light source is a light emitting diode (LED). In some embodiments, the system comprises a light source that excites the bio-ink. In some embodiments, the system comprises a light source that excites a cell in the bio-ink. In some embodiments, the system comprises a light source that excites one or more components of the bio-ink. In some embodiments, one or more components of the bio-ink are detectable. In some embodiments, the components of the bio-ink, that are excited by the light source, comprise a plurality of cells, a protein, a cell adhesion molecule, an extracellular matrix component, a growth factor, an enzyme, a therapeutic agent, a natural polymer, a synthetic polymer, a hydrogel, a nanoparticle, a biochemical factor, a cross-linking agent, a photoinitiator, an additional agent, or a combination thereof. In some embodiments, the plurality of cells excited by the light source is labeled with a fluorescent probe, a fluorescent tag, an affinity tag, or a peptide. In some embodiments, the plurality of cells excited by the light source is a plurality of: chondrocytes, chondrogenic precursors, chondroprogenitors, stem cells, pluripotent stem cells, induced pluripotent stem cells, mesenchymal stem cells, or any combination thereof. In some embodiments, the system comprises a light source to excite a protein in the bio-ink. In some embodiments, the protein excited by the light source is labeled with a fluorescent probe, a fluorescent tag, an affinity tag, or a peptide. In some embodiments, the protein excited by the light source autofluoresces. In some embodiments, the autofluorescent protein that is excited by the light source is collagen.

In some embodiments, the light source emits light with a visible wavelength of to 400 nm to 700 nm. In some embodiments, the light source emits light at a wavelength between about 270 nm to about 370 nm. In some embodiments, the light source emits light at a wavelength between about 480 nm to about 500 nm. In some embodiments, the light source emits light at a wavelength of about 488 nm. In some embodiments, the light source emits light at a wavelength between about 540 nm to about 570 nm. In some embodiments, the light source emits light at a wavelength of about 561 nm. In some embodiments, the light source emits light at a wavelength of about 546 nm. In some embodiments, the light source emits light at a wavelength between about 620 nm to about 640 nm. In some embodiments, the light source emits light at a wavelength of about 633 nm. In some embodiments, the light source emits light at a wavelength between about 640 nm to about 660 nm. In some embodiments, the light source emits light at a wavelength of about 647 nm.

Sensors

In some embodiments, the systems disclosed herein comprise a sensor. In some embodiments, the systems disclosed herein comprise a plurality of sensors. In some embodiments, the sensor is configured to detect and monitor the position of the robotic arm. In some embodiments, the sensor is configured to detect and monitor the position of the bioprinter. In some embodiments, the sensor is configured to detect and monitor the position of the printhead. In some embodiments, the sensor is configured to detect and monitor the position of a nozzle or a plurality of nozzles. In some embodiments, the sensor is configured to detect and monitor the position of a needle. In some embodiments, the sensor is an optical sensor, a rotary encoder, a piezoelectric accelerometer, a capacitive displacement sensor, a gyroscopic sensor, a pressure sensor, an infrared sensor, a linear potentiometer, a stretch sensor, a stereo camera system, a localization system, a light sensor, a thermal sensor, a temperature sensor, a thermal camera, an inertial measurement unit (IMU), a current sensor, a voltage sensor, a magnetic sensor, an electromagnetic sensor, a depth sensor, an acoustic sensor, a touch sensor, a confocal displacement sensor, or any combination thereof.

In some embodiments, the sensor detects the temperature of the bio-ink. In some embodiments, the sensor detects the volume of bio-ink being ejected from the bioprinter. In some embodiments, the sensor detects the degree of rotation of a joint in the robotic arm. In some embodiments, the sensor detects the translation of the robotic arm. In some embodiments, the sensor detects a distance from the bioprinter to the substrate. In some embodiments, the sensor detects a distance from the bioprinter to the tissue defect. In some embodiments, the sensor detects a distance within a substrate. In some embodiments, the sensor detects a distance within a tissue defect. In some embodiments, the sensor provides location feedback to the control system. In some embodiments, the sensor measures a depth of the bio-ink construct. In some embodiments, the sensor measures a depth of the tissue defect. In some embodiments, the sensor measures a temperature of the bio-ink or of the bio-ink construct. In some embodiments, the sensor measures a temperature of the tissue defect.

Endoscopes

In some embodiments, the systems disclosed herein comprise at least one endoscope. In some embodiments, the endoscope is positioned within proximity of the internal tissue defect. In some embodiments, the endoscope visualizes the internal tissue defect during bioprinting. In some embodiments, the endoscope is an arthroscope, bronchoscope, colonoscope, colposcope, cystoeurethroscope, cystoscope, duodenoscope, enteroscope, esophagogastroduodenoscope, fetoscope, gastroscope, gynoscope, hysteroscope, laparoscope, laryngoscope, peritoneoscope, proctosigmoidoscope, sigmoidoscope, thoracoscope, or ureteroscope. In some embodiments, the system comprises a first endoscope, a second endoscope, a third endoscope, a fourth endoscope, or a fifth endoscope within proximity of the internal tissue defect.

In some embodiments, the system comprises an endoscope to detect or visualize the bio-ink during or after bio-printing. In some embodiments, the system comprises an endoscope configured to provide an image of the internal tissue defect, wherein the image is used to provide feedback regarding the structure of a bio-ink construct during a bio-printing process in real time. In some embodiments, the endoscope provides feedback regarding the structure of the bio-construct during the bio-printing process in real time. In some embodiments, the system comprises an endoscope to detect or visualize one or more components of the bio-ink. In some embodiments, the components of the bio-ink comprise a plurality of cells, a protein, a cell adhesion molecule, an extracellular matrix component, a growth factor, an enzyme, a therapeutic agent, a natural polymer, a synthetic polymer, a hydrogel, a nanoparticle, a biochemical factor, a cross-linking agent, a photoinitiator, an additional agent, or a combination thereof. In some embodiments, the system comprises an endoscope to detect or visualize a plurality of cells in the bio-ink. In some embodiments, the plurality of cells detected or visualized by the endoscope is labeled with a fluorescent probe, a fluorescent tag, an affinity tag, or a peptide. In some embodiments, the plurality of cells detected or visualized by the endoscope is a plurality of: chondrocytes, chondrogenic precursors, chondroprogenitors, stem cells, pluripotent stem cells, induced pluripotent stem cells, mesenchymal stem cells, or any combination thereof.

In some embodiments, the system comprises an endoscope to detect or visualize a protein in the bio-ink. In some embodiments, the protein detected or visualized by the endoscope is labeled with a fluorescent probe, a fluorescent tag, an affinity tag, or a peptide. In some embodiments, the protein detected or visualized by the second endoscope autofluoresces. In some embodiments, the autofluorescent protein detected or visualized by the endoscope is collagen. In some embodiments, the autofluorescent collagen comprises collagen type I, collagen type IL collagen type Ill, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, collagen type XXIX or a combination thereof.

In some embodiments, the system comprises at least a first endoscope and a second endoscope, wherein the first endoscope detects or visualizes a first bio-ink during or after bio-printing, and the second endoscope detects or visualizes a second bio-ink during or after bio-printing. In some embodiments, the first bio-ink is different from the second bio-ink. In some embodiments, the first bio-ink and the second bio-ink are the same. In some embodiments, the system comprises at least a first endoscope and a second endoscope, wherein the first endoscope detects or visualizes a first component of a first bio-ink during or after bio-printing, and the second endoscope detects or visualizes a second component of a second bio-ink during or after bio-printing. In some embodiments, the system comprises at least a first endoscope and a second endoscope, wherein the first endoscope detects or visualizes a first component of a first bio-ink during or after bio-printing, and the second endoscope detects or visualizes a second component of the first bio-ink during or after bio-printing. In some embodiments, the first component and the second component are the same. In some embodiments, the first component and the second component are different. In some embodiments, there are additional endoscopes (e.g., third, fourth, fifth endoscope) that detect or visualize additional bio-inks or additional components of bio-inks.

3D Scanners

In some embodiments, the systems disclosed herein comprise a three dimensional (3D) scanner. In some embodiments, the 3D scanner is a three dimensional laser scanner. In some embodiments, the 3D scanner is a hand-held laser scanner. In some embodiments, the 3D scanner is a three dimensional X-ray scanner. In some embodiments, the 3D scanner is a structured light three dimensional. In some embodiments, the 3D scanner is a contact 3D scanner. In some embodiments, the 3D scanner is a modulated light 3D scanner. In some embodiments, the 3D scanner is a stationary 3D laser scanner. In some embodiments, the 3D scanner is a time-of-flight 3D scanner. In some embodiments, the time-of-flight is a laser phase-shift 3D scanner or a laser pulsed-based 3D scanner.

In some embodiments, the 3D scanner is located in a flexible, tubular instrument, similar in structure to an endoscope. In some embodiments, the 3D scanner located in close proximity to or in contact with a tissue defect. In some embodiments, the 3D scanner is located in close proximity to or in contact with an osteochondral defect. In some embodiments, the 3D scanner is located in close proximity to or in contact with a chondral defect.

In some embodiments, the 3D scanner scans the internal tissue defect. In some embodiments, the 3D scanner scans the bio-ink. In some embodiments, the 3D scanner scans the bio-ink construct. In some embodiments, the 3D scanner creates a point cloud of the internal tissue defect. In some embodiments, a point cloud is a set of data points in a three dimensional coordinate system that is measured and outputted by the 3D scanner. In some embodiments, the 3D scanner creates a point cloud of the internal tissue defect before, during, or after the bioprinting process. In some embodiments, the 3D scanner creates a point cloud of the bio-ink. In some embodiments, the 3D scanner creates a point cloud of the bio-ink construct. In some embodiments, the 3D scanner creates a point cloud of the bio-ink or bio-ink construct before, during, or after the bioprinting process. In some embodiments, the control system uses the point cloud created by the 3D scanner to design a bio-ink construct. In some embodiments, the control system uses the point cloud created by the 3D scanner to direct the bioprinter. In some embodiments, the control system uses the point cloud created by the 3D scanner to determine the bio-ink printing parameters. In some embodiments, the control system uses the point cloud created by the 3D scanner to provide spatial, structural, or geometrical feedback of the bio-ink or bio-ink construct. In some embodiments, the spatial, structural, or geometrical feedback of the bio-ink or bio-ink construct is generated before, during, or after the bioprinting process.

In some embodiments, the 3D scanner provides feedback regarding the structure of the bio-construct during the bio-printing process in real time. In some embodiments, the 3D scanner provides a feedback regarding the location of the bio-construct during the bio-printing process in real time. In some embodiments, the 3D scanner provides a feedback regarding the location of the bio-ink during the bio-printing process in real time. In some embodiments, the feedback provided by the 3D scanner is spatial feedback. In some embodiments, the spatial feedback is calculated by the computing system. In some embodiments, the computing system executes instructions to take a 3D scan of the bio-construct during the bio-printing process. In some embodiments, the computing system executes instructions to take a 3D scan of the substrate or tissue defect during the bio-printing process. In some embodiments, the computing system executes instructions to take a 3D scan of the bio-construct during the bio-printing process, compare it to the original design to be printed of the bio-construct structure, and detect any structural differences between them. In some embodiments, the computing system executes instructions to take a first 3D scan of the substrate or tissue defect, take a second 3D scan of the substrate or tissue defect during the bio-printing process, compare the first and second 3D scans, and detect any differences between the first and second scan.

In some embodiments, the 3D scanner provides an image of the internal tissue defect. In some embodiments, the 3D scanner provides an image of the internal tissue defect that is used to design a bio-ink construct. In some embodiments, the 3D scanner provides an image of the internal tissue defect that is used to determine the shape or structure of the bio-ink construct. In some embodiments, the 3D scanner provides an image of the internal tissue defect that is used to design a bio-ink construct that fits or aligns with a tissue defect of a patient. In some embodiments, the 3D scanner provides an image of the internal tissue defect that is used to design a bio-ink construct that is patient specific. In some embodiments, the 3D scanner provides an image of the internal tissue defect that is used to design a bio-ink construct that matches the shape or construct of the tissue defect of the patient. In some embodiments, the 3D scanner provides an image of the internal tissue defect that is used to design a bio-ink construct that complements the shape or construct of the tissue defect of the patient. In some embodiments, the 3D scanner provides an image of the internal tissue defect that is used by the control system to determine the instructions to be sent to the bioprinter. In some embodiments, the 3D scanner provides an image of the internal tissue defect that is used by the control system to determine the bio-ink printing parameters.

In some embodiments, the 3D scanner provides a point cloud of the internal tissue defect. In some embodiments, the 3D scanner provides a point cloud of the internal tissue defect that is used to design a bio-ink construct. In some embodiments, the 3D scanner provides a point cloud of the internal tissue defect that is used to determine the shape or structure of the bio-ink construct. In some embodiments, the 3D scanner provides a point cloud of the internal tissue defect that is used to design a bio-ink construct that fits or aligns with a tissue defect of a patient. In some embodiments, the 3D scanner provides a point cloud of the internal tissue defect that is used to design a bio-ink construct that is patient specific. In some embodiments, the 3D scanner provides a point cloud of the internal tissue defect that is used to design a bio-ink construct that matches the shape or construct of the tissue defect of the patient. In some embodiments, the 3D scanner provides a point cloud of the internal tissue defect that is used to design a bio-ink construct that complements the shape or construct of the tissue defect of the patient. In some embodiments, the 3D scanner provides a point cloud of the internal tissue defect that is used by the control system to determine the instructions to be sent to the bioprinter. In some embodiments, the 3D scanner provides a point cloud of the internal tissue defect that is used by the control system to determine the bio-ink printing parameters.

Uses of Compositions and Methods

Provided herein are compositions and methods for treating a subject in need thereof. In some embodiments, the subject is a burn victim, an athlete or an amputee. In some embodiments, the subject is an elderly individual, an infant, or a youth. In some embodiments, the subject is in need of an organ transplant. In some embodiments, the subject in need of an organ transplant requires an eye, a heart, a lung, a stomach, an intestine, a colon, a bladder, a pancreas, a spleen, a uterus, an ovary, a prostate, a muscle, a bone, an artery, a blood vessel, a thyroid, a liver or a kidney. In some embodiments, the subject suffers from an autoimmune disease, a cardiovascular disorder, an autophageal disorder or a neurodegenerative disorder. In some embodiments, the neurodegenerative disorder is selected from Parkinson's Disease, Alzheimer's Disease, Huntington's Disease, Amyotrophic Lateral Sclerosis (Lou Gehrig's Disease), or macular degeneration. In some embodiments, the autoimmune disease is selected from multiple sclerosis, encephalomyelitis, hepatitis, inner ear disease, peripheral neuropathy or pancreatitis. In some embodiments, the subject is suffering from brain trauma, tissue degeneration, cancer, arthritis, osteoarthritis, gout, tooth decay or an ulcer. In some embodiments, subject suffers from osteoarthritis. In some embodiments, the subject is a human. In some embodiments, the subject is an animal. In further embodiments, the animal is under the care of an owner, caretaker, rescuer, or veterinarian. In still further embodiments, the animal is an invertebrate, fish, amphibian, reptile, bird, or mammal.

Provided herein are compositions and methods for treating an internal defect of a subject in need thereof. In some embodiments, the internal tissue defect is located in or on a tissue or organ selected from a vascular tissue, an osteochondral tissue, an epidermal tissue, a muscular tissue, an intestinal tissue, a neuronal tissue, a reproductive tissue, a pancreatic tissue, an ocular tissue, an ear, an eye, a cornea, a nose, a brain, a sinus, a tooth, a bone, cartilage, skin, an esophagus, a trachea, a thymus, a thyroid, a heart, a blood vessel, a lung, a diaphragm, a lymph node, a breast, a nipple, a stomach, an intestine, a colon, a rectum, a pancreas, a spleen, a bladder, a kidney, a liver, an ovary, a uterus, a vagina, a prostate, a penis, a cervix, adipose, skeletal muscle, smooth muscle or skin. In some embodiments, the skin is located on a head, on a face, on a neck, on a shoulder, on a chest, on an arm, on a hand, on a back, on a buttock, on a leg, on an ankle or on a foot. In some embodiments, the method comprises treating an internal tissue defect in a joint. In some embodiments, the joint is located in a neck, a shoulder, a back, a spine, a chest, an arm, a hand, an elbow, a wrist, a finger, a leg, an ankle, a foot, a hip or a knee. In some embodiments, the joint is located in a knee.

In some embodiments, the internal tissue defect is a birth defect or a congenital defect. In some embodiments, the internal tissue defect is a result of an injury. In some embodiments, the injury is due to musculoskeletal trauma, a sport injury, an automobile accident, an infection, or a tumor. In some embodiments, the method comprises treating an internal tissue defect wherein the internal tissue defect is selected from a damaged tissue, eroded tissue, diseased tissue or degenerated tissue. In some embodiments, the damaged tissue is selected from a tissue damaged by a burn, an abrasion, a tear, a lesion, a break, a fracture, a bruise, a hematoma, a scratch, a cut, a puncture, an infection, a tumor, frostbite, overuse or necrosis. In some embodiments, the method comprises characterization of the internal tissue defect. In some embodiments, the method comprises x-ray, CAT/CT scan, PET scan, MRI, ultrasound, thermography, endoscopy, radiography or biopsy of the internal tissue defect. In some embodiments, the method comprises preparation of the internal tissue defect before surgery. In some embodiments, preparation of the internal tissue defect comprises tissue removal, radiation, sterilization, cleaning, treatment with an antibiotic or treatment with an anesthetic.

In some embodiments, the tissue defect is an articular joint defect. In some embodiments, the tissue defect is a chondral defect. In some embodiments, a chondral defect is a focal area of injury or damage to articular cartilage. In some embodiments, the tissue defect is an osteochondral defect. In some embodiments, an osteochondral defect is a focal area of injury or damage to articular cartilage in combination with damage or injury to adjacent subchondral bone. In some embodiments, the tissue defect is a tissue defect in the knee, a tissue defect in the hip, a tissue defect in the shoulder, a tissue defect in the ankle, or a tissue defect in the elbow. In some embodiments, the tissue defect is a fractured bone. In some embodiments, the tissue defect is a fracture in the knee, a fracture in the hip, a fracture in the shoulder, a fracture in the ankle, or a fracture in the elbow. In some embodiments, the tissue defect is a torn ligament. In some embodiments, the tissue defect is a torn ligament in the knee, a torn ligament in the hip, a torn ligament in the shoulder, a torn ligament in the ankle, or a torn ligament in the elbow. In some embodiments, the tissue defect is a torn tendon. In some embodiments, the tissue defect is a torn tendon in the knee, a torn tendon in the hip, a torn tendon in the shoulder, a torn tendon in the ankle, or a torn tendon in the elbow. In some embodiments, the tissue defect is a swollen synovium. In some embodiments, the tissue defect is a torn articular cartilage. In some embodiments, the tissue defect is a meniscal cartilage tear. In some embodiments, the tissue defect is a surface cartilage tear. In some embodiments, the tissue defect is a torn meniscus. In some embodiments, the tissue defect is a knee bone fracture. In some embodiments, the tissue defect is a torn anterior cruciate ligament or a torn posterior cruciate ligament. In some embodiments, the tissue defect is a Baker's cyst. In some embodiments, the tissue defect is a tear on the labrum.

The disclosure is further understood through review of the numbered embodiments recited herein. Various embodiments contemplated herein may include, but need not be limited to, one or more of the following, and combinations thereof:

1. A method of bioprinting a bio-ink construct on an internal tissue defect during a minimally invasive surgery on an individual in need thereof, comprising: a. visualizing the internal tissue defect; b. positioning a bioprinter comprising a printhead within proximity of or in contact with the internal tissue defect; and c. ejecting a bio-ink from the printhead onto the internal tissue defect to form a bio-ink layer, thereby generating a bio-ink construct. 2. The method of claim 1, wherein the bio-ink construct comprises a plurality of bio-ink layers. 3. The method of claim 1, wherein the bio-ink construct is a live tissue. 4. The method of claim 1, wherein the printhead comprises a needle, an extended cylinder, a fluid line, a print nozzle, or a plurality of print nozzles. 5. The method of claim 4, wherein each print nozzle of the plurality of print nozzles is independently controlled and actuated. 6. The method of claim 4, wherein each print nozzle of the plurality of print nozzles is actuated to eject an individual droplet of the bio-ink. 7. The method of claim 6, wherein the plurality of print nozzles ejects the individual droplet simultaneously. 8. The method of claim 6, wherein the plurality of print nozzles ejects the individual droplet in a specified sequence. 9. The method of claim 1, wherein the printhead ejects the bio-ink continuously. 10. The method of claim 1, wherein the bio-ink comprises a plurality of cells, a component of extracellular matrix, a synthetic polymer, a natural polymer, a cross-linking agent, a photoinitiator, or a combination thereof 11. The method of claim 10, wherein the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, kidney cells, hepatic cells, pancreatic cells, immune cells, stem cells, germ cells, nurse cells, interstitial cells, stellate cells and progenitors thereof 12. The method of claim 10, wherein the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, and progenitors thereof 13. The method of claim 10, wherein the plurality of cells comprises chondrocytes. 14. The method of claim 10, wherein the component of extracellular matrix comprises collagen, elastin, fibrillin, fibronectin, laminin, fibrinogen, tenascin, thrombospondin, integrin, hyaluronic acid, heparin, heparin sulfate, chondroitin sulfate, keratin sulfate, dermatan sulfate, or a combination thereof 15. The method of claim 10, wherein the synthetic polymer is polyethylene glycol (PEG), a PEG macromere, polyethylene glycol methacrylate (PEGMA), polyethylene dimethacrylate (PEDGMA), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide, or a combination thereof. 16. The method of claim 10, wherein the natural polymer is alginate, cellulose, gelatin, pectin, agarose, chitosan, or a combination thereof. 17. The method of claim 10, wherein the cross-linking agent comprises calcium chloride, calcium sulfate, calcium carbonate, calcium (Ca2+), magnesium (Mg2+), glutaraldehyde, genipin, nordihydroguaiaretic acid, tannin acid, procyanidins, glycosaminoglycan (GAG), 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), or a combination thereof. 18. The method of claim 1, further comprising polymerizing the bio-ink. 19. The method of claim 18, wherein polymerizing the bio-ink comprises cross-linking the bio-ink. 20. The method of claim 19, wherein cross-linking the bio-ink comprises delivering the cross-linking agent by the printhead to the bio-ink. 21. The method of claim 19, wherein cross-linking the bio-ink comprises applying UV light from a light source to the bio-ink. 22. The method of claim 19, wherein cross-linking the bio-ink comprises applying heat to the bio-ink. 23. The method of claim 1, wherein the bioprinter comprises a second printhead. 24. The method of claim 1, further comprising positioning a second bioprinter comprising a printhead within proximity of or in contact with the internal tissue defect. 25. The method of claim 24, further comprising ejecting a second bio-ink from the printhead of the second bioprinter onto the internal tissue defect to form a second bio-ink layer. 26. The method of claim 1, further comprising controlling the bioprinter with a control system. 27. The method of claim 26, wherein the control system comprises a computer system. 28 The method of claim 27, wherein the control system comprises a robotic arm operatively connected to the computer system. 29. The method of claim 28, wherein the robotic arm is coupled to a body part of the individual. 30. The method of claim 28, wherein the robotic arm positions the bioprinter. 31. The method of claim 30, wherein the bioprinter is moved along an X, Y, or Z axis, or a combination thereof 32. The method of claim 30, wherein the bioprinter is rotated around the X, Y, or Z axis, or a combination thereof 33. The method of claim 26, wherein the control system controls a bio-ink printing parameter. 34. The method of claim 33, wherein the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof. 35. The method of claim 1, wherein visualizing the internal tissue defect occurs before, during, or after ejecting the bio-ink. 36. The method of claim 1, wherein visualizing the internal tissue defect comprises imaging the internal tissue defect. 37. The method of claim 1, further comprising positioning an endoscope within proximity of the internal tissue defect. 38. The method of claim 37, wherein the endoscope visualizes the internal tissue defect. 39. The method of claim 1, wherein the internal tissue defect is selected from a damaged tissue, eroded tissue, diseased tissue or degenerated tissue. 40. The method of claim 1, wherein the internal tissue defect is in an internal tissue selected from bone, muscle, nerves, brain, eye, pancreas, spleen, cartilage, thyroid, adipose, sinus, esophagus, kidney, heart, lung, intestine, stomach, colon, rectum, breast, ovary, uterus, cervix, prostate, bladder or liver. 41. The method of claim 1, wherein the internal tissue defect is selected from a vascular defect, a chondral defect, a muscular defect, an intestinal defect, a neuronal defect, a reproductive defect, a pancreatic defect, or an ocular defect. 42. The method of claim 1, wherein the internal tissue defect comprises a chondral defect. 43. The method of claim 42, wherein the chondral defect is in a joint selected from a knee joint, a hip joint, an elbow joint, a shoulder joint, a wrist joint, a spine joint, a finger joint, an ankle joint, or a foot joint. 44. The method of claim 42, wherein the chondral defect is in a knee joint. 45. The method of claim 42, wherein the chondral defect is an osteochondral defect. 46. A method of bioprinting a bio-ink construct on a chondral defect during a minimally invasive surgery on an individual in need thereof comprising: a. visualizing the chondral defect; b. positioning a bioprinter comprising a printhead within proximity of or in contact with the chondral defect; and c. ejecting a bio-ink from the printhead onto the chondral defect to form a bio-ink layer, thereby generating a bio-ink construct. 47. The method of claim 46, wherein the bio-ink construct comprises a plurality of bio-ink layers. 48. The method of claim 46, wherein the bio-ink construct is a live tissue. 49. The method of claim 1, wherein the printhead comprises a needle, an extended cylinder, a fluid line, a print nozzle, or a plurality of print nozzles. 50. The method of claim 49, wherein each print nozzle of the plurality of print nozzles is independently controlled and actuated. 51. The method of claim 49, wherein each print nozzle of the plurality of print nozzles is actuated to eject an individual droplet of the bio-ink. 52. The method of claim 51, wherein the plurality of print nozzles ejects the individual droplet simultaneously. 53. The method of claim 51, wherein the plurality of print nozzles ejects the individual droplet in a specified sequence. 54. The method of claim 1, wherein the printhead ejects the bio-ink continuously. 55. The method of claim 46, wherein the bio-ink comprises a plurality of cells, a component of extracellular matrix, a synthetic polymer, a natural polymer, a cross-linking agent, a photoinitiator, or a combination thereof 56. The method of claim 55, wherein the plurality of cells comprises cells selected from chondrocytes, connective tissue fibroblasts, tendon fibroblasts, bone marrow reticular tissue fibroblasts, non-epithelial fibroblasts, pericytes, osteoprogenitor cells, osteoblasts, osteoclasts, and progenitors thereof 57. The method of claim 55, wherein the plurality of cells comprises chondrocytes. 58. The method of claim 55, wherein the component of extracellular matrix comprises collagen, elastin, fibrillin, fibronectin, laminin, fibrinogen, tenascin, thrombospondin, integrin, hyaluronic acid, heparin, heparin sulfate, chondroitin sulfate, keratin sulfate, dermatan sulfate, or a combination thereof 59. The method of claim 55, wherein the synthetic polymer is polyethylene glycol (PEG), a PEG macromere, polyethylene glycol methacrylate (PEGMA), polyethylene dimethacrylate (PEDGMA), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide, or a combination thereof 60. The method of claim 55, wherein the natural polymer is alginate, cellulose, gelatin, pectin, agarose, chitosan, or a combination thereof. 61. The method of claim 55, wherein the cross-linking agent comprises calcium chloride, calcium sulfate, calcium carbonate, calcium (Ca2+), magnesium (Mg2+), glutaraldehyde, genipin, nordihydroguaiaretic acid, tannin acid, procyanidins, glycosaminoglycan (GAG), 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), or a combination thereof 62. The method of claim 46, further comprising polymerizing the bio-ink. 63. The method of claim 46, wherein polymerizing the bio-ink comprises cross-linking the bio-ink. 64. The method of claim 63, wherein cross-linking the bio-ink comprises delivering the cross-linking agent by the printhead to the bio-ink. 65. The method of claim 63, wherein cross-linking the bio-ink comprises applying UV light from a light source to the bio-ink. 66. The method of claim 63, wherein cross-linking the bio-ink comprises applying heat to the bio-ink. 67. The method of claim 46, wherein the bioprinter comprises a second printhead. 68. The method of claim 67, further comprising positioning a second bioprinter comprising a printhead within proximity of or in contact with the chondral defect. 69. The method of claim 68, further comprising ejecting a second bio-ink from the printhead of the second bioprinter onto the chondral defect to form a second bio-ink layer. 70. The method of claim 46, further comprising controlling the bioprinter with a control system. 71. The method of claim 70, wherein the control system comprises a computer system. 72. The method of claim 71, wherein the control system comprises a robotic arm operatively connected to the computer system. 73. The method of claim 72, wherein the robotic arm is coupled to a body part of the individual. 74. The method of claim 73, wherein the robotic arm positions the bioprinter. 75. The method of claim 74, wherein the bioprinter is moved along an X, Y, or Z axis, or a combination thereof 76. The method of claim 74, wherein the bioprinter is rotated around the X, Y, or Z axis, or a combination thereof. 77. The method of claim 71, wherein the control system controls a bio-ink printing parameter. 78. The method of claim 77, wherein the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof. 79. The method of claim 46, wherein visualizing the chondral defect occurs before, during, or after ejecting the bio-ink. 80. The method of claim 46, wherein visualizing the chondral defect comprises imaging the chondral defect. 81. The method of claim 46, further comprising positioning an endoscope within proximity of the chondral defect. 82. The method of claim 81, wherein the endoscope visualizes the chondral defect. 83. The method of claim 46, wherein the chondral defect is selected from a damaged tissue, eroded tissue, diseased tissue or degenerated tissue. 84. The method of claim 46, wherein the chondral defect is in a joint selected from a knee joint, a hip joint, an elbow joint, a shoulder joint, a wrist joint, a spine joint, a finger joint, an ankle joint, or a foot joint. 85. The method of claim 46, wherein the chondral defect is in a knee joint. 86. The method of claim 46, wherein the chondral defect is an osteochondral defect. 87. A system for bioprinting a bio-ink construct on an internal tissue defect during a minimally invasive surgery on an individual in need thereof, comprising a control system, an endoscope, and a bioprinter comprising a printhead. 88. The system of claim 87, further comprising a light source. 89. The system of claim 87, wherein the printhead comprises a needle, an extended cylinder, a fluid line, a print nozzle, or a plurality of print nozzles. 90. The system of claim 87, wherein the bioprinter comprises a second printhead. 91. The system of claim 87, further comprising a second bioprinter. 92. The system of claim 87, wherein the control system controls the bioprinter. 93. The system of claim 87, wherein the control system comprises a computer system. 94. The system of claim 93, wherein the control system comprises a robotic arm operatively connected to the computer system. 95. The system of claim 94, wherein the robotic arm is coupled to a body part. 96. The system of claim 94, wherein the robotic arm positions the bioprinter. 97. The system of claim 96, wherein the bioprinter is moved along an X, Y, or Z axis, or a combination thereof 98. The system of claim 96, wherein the bioprinter is rotated around the X, Y, or Z axis, or a combination thereof 99. The system of claim 87, wherein the control system controls a bio-ink printing parameter. 100. The system of claim 99, wherein the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof. 101. The system of claim 100, wherein the firing energy includes pulse energy, pulse width, length of gap between pulses, and voltage. 102. The system of claim 94, wherein the control system comprises a second robotic arm operatively connected to the computer system. 103. The system of claim 102, wherein the robotic arm controls a position of the second bioprinter.

EXAMPLES

Example 1: Repairing a Chondral Defect in the Knee During Surgery, Using a Single Printhead in a Single Bioprinter A 16-year old boy has a chondral defect of the knee joint due to a repetitive sports injury. Healthy human articular cartilage is harvested from the boy and is rinsed and sterilized with phosphate buffered saline (PBS). Sterile scalpels are used to excise articular cartilage from femoral condyles and tibia plateaus under aseptic conditions. Harvested cartilage samples arc minced and treated with 0.5 mg/mL trypsin at 37° C. for 15 min. After removing trypsin solution, the cartilage tissues are digested with 2 mg/mL type IV clostridial collagenase in DMEM with 5% fetal calf serum for 12 h to 16 h at 37° C. Released human articular chondrocytes are washed three times with DMEM supplemented with 1× penicillin-streptomycin-glutamine (PSG) and cell viability is determined. Isolated chondrocytes are seeded into T175 tissue culture flasks at 5 million cells per flask for expansion in monolayer and cultured in DMEM supplemented with 10% calf serum and 1× PSG. Cells are incubated at 37° C. with humidified air containing 5% $CO_2$. The culture medium is changed every 4 days. Human chondrocytes are ready to be used (e.g. bioprinted) when 80% to 90% confluence is reached (1 to 2 weeks in primary culture). All cells used for bioprinting are first or second passage.

During the surgery to repair the chondral defect, a bioprinter is attached to a robotic arm. The bioprinter comprises a syringe. The syringe contains a bio-ink comprising the individual's previously harvested chondrocytes and a hydrogel such as Matrigel®. An endoscope is further placed near the defect in order to monitor, in real time, the bioprinting process, with the surgeon manually adjusting any bioprinting parameter as needed. The surgeon positions the bioprinter, and then engages the control system to begin bioprinting. The bio-rink comprising the chondrocytes and Matrigel® is extruded onto the chondral defect.

Example 2: Repairing an Osteochondral Defect in the Knee During Surgery, Using Four Printheads in a Single Bioprinter During a surgery to repair an osteochondral defect in an individual, a bioprinter is attached to a robotic arm. The bioprinter comprises four printheads. The first printhead comprises the individual's previously harvested chondrocytes. The second printhead comprises the individual's previously harvested osteoblasts. The third printhead comprises alginate. The fourth printhead comprises calcium chloride. All printheads utilize ink-jet based printing and comprise 300 print nozzles, set at a distance of 1 to 2 mm from the osteochondral defect. A combination of the osteoblasts, alginate, and calcium chloride is printed onto the bone defect of the osteochondral defect. A combination of the chondrocytes, alginate, and calcium chloride is then printed onto the cartilage defect of the osteochondral defect.

An endoscope is further placed near the osteochondral defect in order to monitor, in real time, the bioprinting process, with the surgeon manually adjusting any bioprinting parameter as needed. The surgeon positions the bioprinter, and then engages the control system to begin bioprinting.

Example 3: Repairing a Chondral Defect in Knee Cartilage During Surgery, Using UV Cross Linking During a surgery to repair a chondral defect in an individual, a bioprinter comprising a printhead is attached to a robotic arm. Purified PEGDMA is dissolved in PBD to a concentration of 10% w/v. Photoinitiator I-2959 (Irgacure®) is added at a final concentration of 0.05 w/v. The bio-ink is made up of the individual's previously harvested chondrocytes suspended in filter-sterilized PEGDMA solution at $5 \times 10^6$ cells/mL. A UV lamp is attached to an endoscope.

The printhead is set at a distance of 1 to 2 mm from the defect. The endoscope is placed near the defect in order to monitor, in real time, the bioprinting process, with the surgeon manually adjusting any bioprinting parameter as needed. The surgeon positions the bioprinter, and then engages the control system to begin bioprinting. As the bio-ink it being ejected, it is exposed to UV light emitted from the UV lamp at a wavelength of 280 nm, thereby cross-linking the PEDGMA.

Example 4: Repairing an Osteochondral Defect in the Knee During Surgery, Using UV Crosslinking During a surgery to repair an osteochondral defect in an individual, a bioprinter comprising two printheads is attached to a robotic arm. The printheads of the bioprinter comprises 300 print nozzles, set at a distance of 1 to 2 mm from the defect. The first printhead contains a bio-ink comprising an individual's previously harvested chondrocytes, a methacrylated hyaluronic acid (MeHA), and the photoinitiator 1-2959 (Irgacure®). The second printhead contains a bio-ink comprising an individual's previously harvested osteoblasts, a methacrylated hyaluronic acid (MeHA), and the photoinitiator I-2959 (Irgacure®). An endoscope is placed near the osteochondral defect in order to monitor, in real time, the bioprinting process, with the surgeon manually adjusting any bioprinting parameter as needed. The surgeon positions the bioprinter, and then engages the control system to begin bioprinting. Several layers of the bio-ink comprising the osteoblasts are applied to the osteochondral defect first, followed by several layers of the bio-ink comprising the chondrocytes. A UV lamp attached to the endoscope emits UV light at 280 nm onto the area while the bio-ink construct is being printed, thereby crosslinking the construct.

Example 5: Repairing an Osteochondral Defect in the Knee During Surgery, Using a Robotic Arm Controlled by a Surgeon During a surgery to repair an osteochondral defect in an individual, a bioprinter comprising printheads, is attached to a robotic arm. An endoscope is placed near the osteochondral defect in order to monitor, in real time, the bioprinting process, with the surgeon manually adjusting any bioprinting parameter as needed. The surgeon positions the bioprinter, and then engages the control system to begin bioprinting. The robotic arm only prints when the printhead is pointing at the target and turns off if moved away from the target area. Several layers of the bio-ink comprising a plurality of osteoblasts is applied to the osteochondral defect first, followed by several layers of the bio-ink comprising a plurality of chondrocytes. The control system turns on the printhead with the appropriate cell type when printing each layer (i.e. the control system turns on a first printhead loaded with the bio-ink comprising osteoblasts only when printing the bone layer and the control system turns on a second printhead loaded with the bio-ink comprising chondrocytes only when printing the cartilage layer). A UV lamp attached to the endoscope emits UV light at 280 nm onto the area while the bio-ink construct is being printed, thereby cross-linking the construct. Having the surgeon control the motion of the robotic arm increases safety and reduces the need for a mechanical actuation of the robotic arm. The robotic control of the printheads ensures that cells are only printed at the desired location.

Example 6: Repairing an Osteochondral Defect in the Knee During Surgery, Using a Robotic Arm Controlled by a Computer During a surgery to repair an osteochondral defect in an individual, a bioprinter comprising printheads is attached to a robotic arm. An endoscope is placed near the osteochondral defect in order to monitor, in real time, the bioprinting process, with the surgeon manually adjusting any bioprinting parameter as needed. The surgeon positions the bioprinter, and then engages the control system to begin bioprinting. The control system controls the motion of the robotic arm through actuators and only prints when the printhead is pointing at the target. Several layers of the bio-ink comprising the osteoblasts are applied to the osteochondral defect first, followed by several layers of the bio-ink comprising the chondrocytes. The control system turns on the printhead with the appropriate cell type when printing each layer (i.e. the control system turns on a first printhead loaded with the bio-ink comprising osteoblasts only when printing the bone layer and the control system turns on a second printhead loaded with the bio-ink comprising chondrocytes only when printing the cartilage layer). A computerized visual feedback system provides real time imaging of the defect being printed and controls the motion of the robotic arm and the firing of the printheads to account for errors in printing or missed print areas. A UV lamp attached to the endoscope emits UV light at 280 nm onto the area while the bio-ink construct is being printed, thereby crosslinking the construct. Having the control system control the motion of the robotic arm increases accuracy when following a preoperative plan. The robotic control of the printheads ensures that cells are only printed at the desired location.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of bioprinting a bio-ink construct on an internal tissue defect during a minimally invasive surgery on an individual in need thereof, comprising:
   a. visualizing the internal tissue defect;
   b. positioning a bioprinter comprising: a printhead, a bio-ink reservoir, and a nozzle within proximity of or in contact with the internal tissue defect, wherein the bio-ink reservoir is fluidically connected to the nozzle, and wherein the bio-ink reservoir contains a bio-ink comprising a plurality of cells and a photoinitiator; and
   c. ejecting the bio-ink from the printhead onto the internal tissue defect to form a bio-ink layer, thereby generating a bio-ink construct.

2. The method of claim 1, wherein the bio-ink construct comprises a plurality of bio-ink layers.

3. The method of claim 1, wherein the bio-ink construct is a live tissue.

4. The method of claim 1, wherein the printhead comprises a needle, an extended cylinder, a fluid line, a print nozzle, or a plurality of print nozzles.

5. The method of claim 1, further comprising polymerizing the bio-ink.

6. The method of claim 1, wherein the bioprinter further comprises a second printhead.

7. The method of claim 1, further comprising positioning a second bioprinter comprising a second printhead within proximity of or in contact with the internal tissue defect.

8. The method of claim 1, further comprising ejecting a second bio-ink from the second printhead of the second bioprinter onto the internal tissue defect to form a second bio-ink layer.

9. The method of claim 1, further comprising controlling the bioprinter with a control system.

10. The method of claim 9, wherein the control system controls a bio-ink printing parameter.

11. The method of claim 10, wherein the bio-ink printing parameter comprises temperature, back-pressure, drops per nozzle, frequency of drop rate, number of nozzles in use, firing energy, resolution, viscosity, cell concentration, physiological temperature, speed of printing, or a combination thereof.

12. The method of claim 9, wherein the method further comprises controlling a robotic arm operatively connected to the control system.

13. The method of claim 12, wherein the method comprises controlling the robotic arm to perform at least one of: 1) positioning the bioprinter within proximity of or in contact with the internal tissue defect, and 2) moving the bioprinter with six degrees of freedom.

14. The method of claim 4, wherein the method further comprises controlling and actuating a first print nozzle of the plurality of print nozzles independently of controlling and actuating a second print nozzle of the plurality of print nozzles.

15. The method of claim 1, wherein the printhead ejects the bio-ink continuously.

16. The method of claim 1, further comprising positioning an endoscope within proximity of the internal tissue defect.

17. The method of claim 16, wherein the endoscope visualizes the internal tissue defect.

18. The method of claim 1, wherein the bio-ink further comprises a component of extracellular matrix, a synthetic polymer, a natural polymer, a cross-linking agent or a combination thereof.

19. The method of claim 1, wherein the internal tissue defect comprises a chondral defect.

20. The method of claim 19, wherein the chondral defect comprises an osteochondral defect.

* * * * *

UNITED STATES PATENT AND TRADEMARK OFFICE
CERTIFICATE OF CORRECTION

PATENT NO. : 12,245,740 B2
APPLICATION NO. : 18/045377
DATED : March 11, 2025
INVENTOR(S) : Darryl D. D'Lima and Clifford W. Colwell, Jr.

Page 1 of 1

It is certified that error appears in the above-identified patent and that said Letters Patent is hereby corrected as shown below:

In the Claims

Column 48, Line 60 "a bio-ink construct." should read --the bio-ink construct.--

Column 49, Line 8 "The method of claim 1," should read --The method of claim 7,--

Signed and Sealed this
Twenty-second Day of April, 2025

Coke Morgan Stewart
*Acting Director of the United States Patent and Trademark Office*